United States Patent
Torgerson

(10) Patent No.: US 12,090,325 B2
(45) Date of Patent: Sep. 17, 2024

(54) MANAGEMENT OF ELECTRICAL STIMULATION THERAPY

(71) Applicant: Medtronic, Inc., Minneapolis, MN (US)

(72) Inventor: Nathan A. Torgerson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 481 days.

(21) Appl. No.: 17/237,840

(22) Filed: Apr. 22, 2021

(65) Prior Publication Data
US 2021/0308463 A1    Oct. 7, 2021

Related U.S. Application Data

(63) Continuation of application No. 16/155,513, filed on Oct. 9, 2018, now Pat. No. 10,987,515.
(Continued)

(51) Int. Cl.
*A61N 1/36*       (2006.01)
*A61N 1/05*       (2006.01)
(Continued)

(52) U.S. Cl.
CPC ....... *A61N 1/36139* (2013.01); *A61N 1/0551* (2013.01); *A61N 1/06* (2013.01);
(Continued)

(58) Field of Classification Search
CPC .............. A61N 1/0551; A61N 1/36139; A61N 1/36034
See application file for complete search history.

(56) References Cited

U.S. PATENT DOCUMENTS 5,603,726 A    2/1997  Schulman et al.
5,800,465 A    9/1998  Thompson et al.
(Continued)

FOREIGN PATENT DOCUMENTS

CN    102921105 B    8/2015
CN    107050645 A    8/2017
(Continued)

OTHER PUBLICATIONS

Ebbini et al., "Monitoring and Guidance of Minimally-Invasive Thermal Therapy Using Diagnostic Ultrasound," 31st Annual International Conference of the IEEE EMBS, Sep. 2-6, 2009, 4 pp.
(Continued)

*Primary Examiner* — Michael J D'Abreu
(74) *Attorney, Agent, or Firm* — Shumaker & Sieffert, P.A.

(57) ABSTRACT

The techniques of the disclosure describe example medical devices, systems, and methods for delivering electrical stimulation therapy to a patient. In one example, a medical device selects subsets of a plurality of therapy parameter sets that define electrical stimulation therapy, each subset including at least one therapy parameter set and less than all of the therapy parameter sets. Further, the medical device delivers, via a plurality of electrodes, electrical stimulation therapy according to each subset via a respective set of electrodes different from sets of electrodes of each other subset of the therapy parameter sets. The medical device iteratively delivers the electrical stimulation therapy according to the subsets of the therapy parameter sets via the respective sets of electrodes. Further, the medical device selects at least one subset of the therapy parameter sets that treat a condition of the patient for defining subsequent delivery of electrical stimulation to the patient.

21 Claims, 8 Drawing Sheets

Related U.S. Application Data

(60) Provisional application No. 62/570,510, filed on Oct. 10, 2017.

(51) Int. Cl.
*A61N 1/06* (2006.01)
*A61N 1/372* (2006.01)

(52) U.S. Cl.
CPC ..... *A61N 1/36034* (2017.08); *A61N 1/36132* (2013.01); *A61N 1/36153* (2013.01); *A61N 1/36157* (2013.01); *A61N 1/36185* (2013.01); *A61N 1/37235* (2013.01); *A61N 1/37247* (2013.01); *A61N 1/36007* (2013.01); *A61N 1/36021* (2013.01)

(56) References Cited

U.S. PATENT DOCUMENTS

| | | |
|---|---|---|
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,333,858 B2 | 2/2008 | Killian et al. |
| 7,577,480 B2 | 8/2009 | Zeijlemaker |
| 7,657,318 B2 | 2/2010 | King et al. |
| 7,689,289 B2 | 3/2010 | King |
| 7,742,810 B2 | 6/2010 | Moffitt et al. |
| 7,792,583 B2 | 9/2010 | Miesel et al. |
| 8,224,453 B2 | 7/2012 | De Ridder |
| 8,359,103 B2 | 1/2013 | Alataris et al. |
| 8,504,150 B2 | 8/2013 | Skelton |
| 8,620,441 B2 | 12/2013 | Greenberg et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 9,002,460 B2 | 4/2015 | Parker |
| 9,138,582 B2 | 9/2015 | Doan et al. |
| 9,155,892 B2 | 10/2015 | Parker et al. |
| 9,339,655 B2 | 5/2016 | Carbunaru |
| 9,381,356 B2 | 7/2016 | Parker et al. |
| 9,386,934 B2 | 7/2016 | Parker et al. |
| 10,525,268 B2 | 1/2020 | Torgerson |
| 10,987,515 B2 | 4/2021 | Torgerson |
| 11,071,863 B2 | 7/2021 | Torgerson |
| 11,083,896 B2 | 8/2021 | Johanek |
| 2003/0204223 A1 | 10/2003 | Leinders et al. |
| 2004/0002635 A1 | 1/2004 | Hargrove et al. |
| 2004/0267333 A1 | 12/2004 | Kronberg |
| 2005/0065575 A1 | 3/2005 | Dobak |
| 2006/0229687 A1 | 10/2006 | Goetz et al. |
| 2007/0067004 A1 | 3/2007 | Boveja et al. |
| 2007/0100388 A1 | 5/2007 | Geber |
| 2008/0221640 A1 | 9/2008 | Overstreet et al. |
| 2009/0036945 A1 | 2/2009 | Chancellor et al. |
| 2009/0204173 A1 | 8/2009 | Fang et al. |
| 2009/0222053 A1 | 9/2009 | Gaunt et al. |
| 2009/0270947 A1 | 10/2009 | Stone et al. |
| 2010/0152817 A1 | 6/2010 | Gillbe |
| 2010/0249875 A1 | 9/2010 | Kishawi et al. |
| 2011/0054570 A1 | 3/2011 | Lane |
| 2011/0071589 A1 | 3/2011 | Starkebaum et al. |
| 2011/0125223 A1 | 5/2011 | Carbunaru et al. |
| 2011/0282412 A1 | 11/2011 | Glukhovsky et al. |
| 2012/0016438 A1 | 1/2012 | Alataris et al. |
| 2012/0130444 A1 | 5/2012 | Wei et al. |
| 2012/0155188 A1 | 6/2012 | Buettner et al. |
| 2012/0197336 A1 | 8/2012 | Su |
| 2012/0197338 A1 | 8/2012 | Su et al. |
| 2012/0296389 A1 | 11/2012 | Fang et al. |
| 2013/0060301 A1 | 3/2013 | Polefko et al. |
| 2013/0079841 A1 | 3/2013 | Su et al. |
| 2013/0110194 A1 | 5/2013 | Wei et al. |
| 2013/0208390 A1 | 8/2013 | Singh et al. |
| 2013/0268021 A1 | 10/2013 | Moffitt |
| 2013/0289664 A1 | 10/2013 | Johanek |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142549 A1 | 5/2014 | Su et al. |
| 2014/0142656 A1 | 5/2014 | Alataris et al. |
| 2014/0142673 A1 | 5/2014 | Alataris et al. |
| 2014/0243924 A1 | 8/2014 | Zhu et al. |
| 2014/0243926 A1 | 8/2014 | Carcieri |
| 2014/0277250 A1* | 9/2014 | Su ................ A61N 1/36007 607/40 |
| 2014/0277267 A1 | 9/2014 | Vansickle et al. |
| 2014/0277281 A1 | 9/2014 | Grandhe |
| 2014/0277282 A1 | 9/2014 | Jaax |
| 2014/0296936 A1 | 10/2014 | Alataris et al. |
| 2014/0364919 A1 | 12/2014 | Doan |
| 2014/0364920 A1 | 12/2014 | Doan et al. |
| 2014/0371813 A1 | 12/2014 | King et al. |
| 2014/0378941 A1 | 12/2014 | Su et al. |
| 2014/0379043 A1 | 12/2014 | Howard |
| 2015/0032181 A1 | 1/2015 | Baynham et al. |
| 2015/0127062 A1 | 5/2015 | Holley et al. |
| 2015/0179177 A1 | 6/2015 | Nagao |
| 2015/0217117 A1 | 8/2015 | Hershey |
| 2015/0335893 A1 | 11/2015 | Parker |
| 2015/0360031 A1 | 12/2015 | Bornzin et al. |
| 2016/0030741 A1 | 2/2016 | Wei et al. |
| 2016/0082265 A1 | 3/2016 | Moffitt et al. |
| 2016/0114166 A1 | 4/2016 | Kaula et al. |
| 2016/0121124 A1 | 5/2016 | Johanek et al. |
| 2016/0136420 A1 | 5/2016 | Brink et al. |
| 2016/0157769 A1 | 6/2016 | Min et al. |
| 2016/0175594 A1 | 6/2016 | Min et al. |
| 2016/0271413 A1 | 9/2016 | Vallejo et al. |
| 2016/0346546 A1 | 12/2016 | Zhu |
| 2017/0209695 A1 | 7/2017 | Solomon |
| 2017/0216587 A1 | 8/2017 | Parker |
| 2018/0056073 A1 | 3/2018 | Torgerson |
| 2018/0110987 A1 | 4/2018 | Parker |
| 2018/0369592 A1 | 12/2018 | Johanek |
| 2018/0369593 A1 | 12/2018 | Johanek |
| 2019/0105499 A1 | 4/2019 | Torgerson |
| 2020/0101294 A1 | 4/2020 | Torgerson |
| 2021/0308463 A1 | 10/2021 | Torgerson |
| 2021/0361949 A1 | 11/2021 | Johanek |

FOREIGN PATENT DOCUMENTS

| | | |
|---|---|---|
| EP | 0679371 A1 | 11/1995 |
| EP | 2396072 B1 | 3/2013 |
| EP | 2756864 A1 | 7/2014 |
| JP | 2007307188 A | 11/2007 |
| WO | 2002009808 A1 | 2/2002 |
| WO | 2010058178 A1 | 5/2010 |
| WO | 2010123704 A | 10/2010 |
| WO | 2011156286 A2 | 12/2011 |
| WO | 2014210065 A1 | 12/2014 |
| WO | 2015000721 A1 | 1/2015 |
| WO | 2015143509 A1 | 1/2015 |
| WO | 2015179177 A1 | 11/2015 |
| WO | 2015179281 A1 | 11/2015 |
| WO | 2016090420 A1 | 6/2016 |
| WO | 2017106503 A1 | 6/2017 |

OTHER PUBLICATIONS

Protopappas et al., "An Ultrasound Wearable System for the Monitoring and Acceleration of Fracture Healing in Long Bones," IEEE Transactions on Biomedical Engineering, vol. 52, No., 9, Sep. 2005, 12 pp.

(56) References Cited

OTHER PUBLICATIONS

Sherman, "Patch Based Ultrasound: A New Dimension in Therapeutic Ultrasound," Profiles in Excellence 2010, Rutgers University Biomechanical Sports Podiatrist, Podiatry Management, Jun./Jul. 2010, 2 pp.

International Search Report and Written Opinion of International Application No. PCT/US2018/055052, mailed Jan. 30, 2019, 13 pp.

International Preliminary Report on Patentability from International Application No. PCT/US2018/055052, mailed Apr. 23, 2020, 7 pp.

North et al., "Spinal Cord Stimulation With Interleaved Pulses: A Randomized, Controlled Trial," Neuromodulation: Technology at the Neural Interface, vol. 10. No. 4, Oct. 2007, pp. 349-357.

Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.

"St. Jude's Prodigy Neurostimulator with Burst Technology," Medgadget, Mar. 20, 2014, 4 pp.

Abejon et al., "Back Pain Coverage with Spinal Cord Stimulation: A Different Treatment for Each Patient," International Neuromodulation Society. Jun. 10, 2015; 567, Abstract Only, 1 pp.

Abeloos et al., "High Density Stimulation as an Alternative to Uncomfortable Cervical Tonic Spinal Cord Stimulation: Case Report," International Neuromodulation Society 12th World Congress, Jun. 11-15, 2015, Abstract Only, 1 pp.

Bhadra et al., "High Frequency Electrical Conduction Block of the Pudendal Nerve," Journal of Neural Eng., IOP Publishing LTD, published Jun. 3, 2006, 14 pp.

Breel et al., "High Density Stimulation: A Novel Programming Paradigm for the Treatment of Chronic Pain," International Neuromodulation Society (INS) 12th World Congress; Jun. 9, 2015, Abstract Only, 1 pp.

Cuellar MD et al., "Effect of High-Frequency Alternating Current on Spinal Afferent Nociceptive Transmission," Neuromodulation: Technology at the Neural Interface; Jul.-Aug. 2013; 16(4): pp. 318-327.

Cui et al., "Spinal Cord Stimulation Attenuates Augmented Dorsal Horn Release of Excitatory Amino Acids in Mononeuropathy via a GABAergic Mechanism," Pain 73, Oct. 1997, pp. 87-95.

Cui et al., "Effect of Spinal Cord Stimulation on Tactile Hypersensitivity in Mononeuropathic Rats is Potentiated by Simultaneous GABA(B) and Adenosine Receptor Activation," Neuroscience Letters 247: Apr. 1998; pp. 183-186.

De Ridder et al., "Burst Spinal Cord Stimulation for Limb and Back Pain," World neurosurgery, Nov. 2013; 80(5):642-649 e641.

De Ridder et al., "Burst Spinal Cord Stimulation: Toward Paresthesia-Free Pain Suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak MD, et al., "High Density Stimulation: a Novel Programming Paradigm for the Treatment of Chronic Back and Leg Pain," Abstracts, International Neuromodulation Society 12th World Congress: Jun. 11-15, 2015, 1 pp.

Gao et al., "Effects of Spinal Cord Stimulation With "Standard Clinical" and Higher Frequencies on Peripheral Blood Flow in Rats," Brain Res. Feb. 8, 2010;1313: pp. 53-61.

Grider et al., "High Frequency (1000 Hz) Stimulation Using Commercially Available Implantable Pulse Generator," North American Neuromodulation Society. Dec. 2013, Abstract Only, 2 pp.

Guan et al., "Spinal Cord Stimulation: Neurophysiological and Neurochemical Mechanisms of Action," Curr Pain Headache Rep DOI 10,1007s11916-014-0260-4, Mar. 2012, pp. 217-225.

Guan et al., "Spinal Cord Stimulation-Induced Analgesia: Electrical Stimulation of Dorsal Column and Dorsal Roots Attenuates Dorsal Horn Neuronal Excitability in Neuropathic Rats," Anesthesiology. Dec. 2010;113(6): pp. 1392-1405.

Holsheimer, "Computer Modelling of Spinal Cord Stimulation and its Contribution to Therapeutic Efficacy," Spinal Cord, Aug. 1998, 36: pp. 531-540.

Hubscher et al., "Convergence and Cross Talk in Urogenital Neural Circuitries," J. Neurophysiol 110: 1997-2005, first published Aug. 7, 2013, 9 pp.

Hunt et al., "The Molecular Dynamics of Pain Control," Nat Rev Neurosci. Feb. 2001; 2(2):83-91.

Kemler et al., "Spinal Cord Stimulation in Patients with Chronic Reflex Sympathetic Dystrophy," N Engl J Med, Aug. 31, 2000; 343(9):618-624.

Kilgore et al., "Reversible Nerve Conduction Block Using Kilohertz Frequency Alternating Current," Neuromodulation. Aug. 2013, pp. 242-255.

Kumar et al., "Spinal Cord Stimulation Versus Conventional Medical Management for Neuropathic Pain: a Multicentre Randomised Controlled Trial in Patients with Failed Back Surgery Syndrome," Pain Jul. 2007; 132(1-2): 179-188.

Likar et al., "High Density Spinal Cord Stimulation: a Multi-Center Experience," Abstracts, International Neuromodulation Society 12th World Congress; Jun. 11-15, 2015, 1 pp.

Maeda et al., "Increased C-Fos Immunoreactivity in the Spinal Cord and Brain Following Spinal Cord Stimulation is Frequency-Dependent," Brain Res. Mar. 9, 2009;1259: pp. 40-50.

Maeda et al., "Low Frequencies, But Not High Frequencies of Bi-Polar Spinal Cord Stimulation Reduce Cutaneous and Muscle Hyperalgesia Induced by Nerve Injury," Pain; Feb. 2008; 138(1): pp. 143-152.

Maggi et al., "Effect of Urethane Anesthesia on the Micturition Reflex in Capsaicin-Treated rats." Journal of the Autonomic Nervous System, Jan. 1990, 30(3): 247-251.

North M.D. et al., "Spinal Cord Stimulation Versus Repeated Lumbosacral Spine Surgery for Chronic Pain: A Randomized, Controlled Trial," Neurosurgery, Jan. 2005; 56(1): 98-106; discussion 106-107.

North et al., "Clinical Outcomes of 1 kHz Subperception Spinal Cord Stimulation (SCS): Results of a Prospective Randomized Controlled Crossover Trial," Abstracts, International Neuromodulation Society, Jun. 2015, 1 pp.

Ranck Jr., et al., "Which Elements Are Excited in Electrical Stimulation of Mammalian Central Nervous System: a Review," Brain Res. Nov. 21, 1975; 98(3): pp. 417-440.

Replogle MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato et al., "Spinal Cord Stimulation Reduces Hypersensitivity Through Activation of Opioid Receptors in a Frequency-Dependent Manner," Eur J Pain. Apr. 17, 2012 (4): pp. 551-561.

Schu et al., "Spinal Cord Stimulation Patterns for the Treatment of Failed Back Surgery Syndrome," Neuromodulation. Apr. 2014; 17(5): pp. 443-450.

Shechter et al., "Conventional and Kilohertz-Frequency Spinal Cord Stimulation Produces Intensity- and Frequency-Dependent Inhibition of Mechnical Hypersensitivity in a Rat Model of Neuropathic Pain," Anesthesiology, Aug. 2013; 119(2): pp. 422-432.

Sluka et al., "High-Frequency, But Not Low-Frequency, Transcutaneous Electrical Nerve Stimulation Reduces Aspartate and Glutamate Release in the Spinal Cord Dorsal Horn," J Neurochem. Oct. 17, 2005; 95(6); pp. 1794-1801.

Smith et al., "Successful Use of High-Frequency Spinal Cord Stimulation Following Traditional Treatment Failure," Stereotact Funct Neurosurg. Apr. 2015; 93(3): pp. 190-193.

Snellings et al., "Effects of Stimulation Site and Stimulation Parameters on Baldder Inhibition by Electrical Nerve Stimulation," BJU International, published Aug. 9, 2011, pp. 136-143.

Song et al., "Efficacy of Kilohertz-Frequency and Conventional Spinal Cord Stimulation in Rat Models of Different Pain Conditions," Neuromodulation Jan. 2014; 17(3): pp. 226-234.

Sweet et al., "High Frequency vs. Burst Stimulation Patterns for Dorsal Column Stimulation: The Importance of Charge," American Association of Neurological Surgeons, Abstract, Apr. 4, 2014, 2 pp.

(56) References Cited

OTHER PUBLICATIONS

Walter et al., "Inhibiting the Hyperreflexic Bladder with Electrical Stimulation in a Spinal Animal Model," Neurourology and Urodynamics, 1993, 12:241-253. Applicant points out in accordance with MPEP 609.04(a) that the 1993 year of publication is sufficiently earlier than the effective U.S. filing date of the present application, and any foreign priority date that the particular month of publication is not in issue.
Wille MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.
Woock et al., "Activation and Inhibition of the Micturition Reflex by Penile Afferents in the Cat," Am J. Physiol Regul Intergre Comp Physiol, published Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2005 year of publication is sufficiently earlier than the effective U.S. filing date of the present application, and any foreign priority date that the particular month of publication is not in issue.
Prosecution History from U.S. Appl. No. 16/155,513, dated Mar. 2, 2020 through Dec. 30, 2020, 48 pp.

\* cited by examiner

MANAGEMENT OF ELECTRICAL STIMULATION THERAPY

This application is a continuation of U.S. application Ser. No. 16/155,513, filed Oct. 9, 2018, which claims the benefit of U.S. Provisional Application No. 62/570,510, filed Oct. 10, 2017. The entire contents of both applications are incorporated herein by reference.

TECHNICAL FIELD

This disclosure generally relates to electrical stimulation therapy, and, more specifically, selection of stimulation parameters that define electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient. Such a set of parameters may be referred to herein as an "electrical stimulation therapy parameter set" or "therapy parameter set."

SUMMARY

In general, the disclosure describes example medical devices, systems, and techniques for delivering a plurality of electrical stimulation therapy programs to a patient via a plurality of electrode combinations from an implantable medical device (IMD), e.g., simultaneously or on a time-interleaved basis. An IMD may deliver electrical stimulation to a plurality of target tissue areas over a portion of the body of the patient via respective electrode combinations to evaluate efficacy of the electrical stimulation for treating a condition of the patient. For example, the electrical stimulation may be configured to suppress one or more symptoms of a disease of the patient (e.g., pain or unwanted sensations). By delivering the electrical stimulation to the plurality of target tissue areas, a clinician may rapidly determine whether the electrical stimulation therapy can be effective for treating the patient (e.g., suppressing one or more symptoms of a disease of the patient) without separately delivering the electrical stimulation to each target tissue area before determining stimulation efficacy.

After determining whether the electrical stimulation is effective for treating the patient, the IMD may separately deliver the electrical stimulation to subsets of the plurality of target tissue areas to determine whether any of the subset of the target tissue areas provides efficacious treatment to the patient. For example, a programmer or the IMD may remove at least one electrode or at least one pair of electrodes (e.g., from the plurality of electrodes used in the electrode combinations that treated each respective target tissue area) such that at least one of the target tissue areas of the plurality of target tissue areas does not receive electrical stimulation. The clinician and/or patient may then evaluate which of these tissue area subsets maintain efficacious therapy. In this fashion, the techniques of the disclosure may determine a primary set of electrodes that delivers electrical stimulation therapy to a tissue area smaller than the collective plurality of target tissue areas while maintaining effective therapy. In turn, the IMD may conserve energy by delivering electrical stimulation therapy via the primary set of electrodes to this smaller tissue area. Such techniques may reduce the power usage required to deliver the electrical stimulation therapy over time while maintaining the desired therapy initially provided by delivery electrical stimulation to the plurality of target tissue areas.

In one example, this disclosure describes a method comprising: delivering, by a medical device via a plurality of electrodes, electrical stimulation therapy according to a plurality of therapy parameter sets to a plurality of respective tissue sites of a patient, the electrical stimulation therapy treating a condition of the patient; subsequent to delivering the electrical stimulation therapy according to the plurality of therapy parameter sets, selecting a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets; iteratively delivering, by the medical device, electrical stimulation therapy according to the subsets of the plurality of therapy parameter sets to the patient via the respective sets of electrodes; receiving, for each of the subsets of the plurality of therapy parameter sets, feedback from the patient indicating whether the subset of the plurality of therapy parameter sets treated the condition of the patient; and selecting, based on the feedback from the patient, at least one subset of the plurality of therapy parameter sets that treat the condition of the patient for defining subsequent delivery of electrical stimulation therapy to the patient.

In another example, this disclosure describes a medical device system comprising: stimulation circuitry of a medical device configured to deliver, via a plurality of electrodes, electrical stimulation therapy according to a plurality of therapy parameter sets to a plurality of respective tissue sites of a patient, the electrical stimulation therapy treating a condition of the patient; and processing circuitry configured to: subsequent to delivering electrical stimulation therapy according to the plurality of therapy parameter sets, select a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets; iteratively control delivery, by the stimulation circuitry of the medical device, of electrical stimulation therapy according to the subsets of the plurality of therapy parameter sets to the patient via the respective sets of electrodes; receive, for each of the subsets of the plurality of therapy parameter sets, feedback from the patient indicating whether the subset of the plurality of therapy parameter sets treated the condition of the patient; and select, based on the feedback from the patient, at least one subset of the plurality of therapy parameter sets that treat the condition of the patient for defining subsequent delivery of electrical stimulation therapy to the patient.

In another example, this disclosure describes a medical device system comprising: means for delivering, via a plurality of electrodes, electrical stimulation therapy according to a plurality of therapy parameter sets to a plurality of respective tissue sites of a patient, the electrical stimulation therapy treating a condition of the patient; means for, subsequent to delivering the electrical stimulation therapy according to the plurality of therapy parameter sets, selecting a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets; means for iteratively delivering electrical stimulation therapy according to the subsets of the plurality of therapy parameter sets to the patient via the respective sets of electrodes; means for receiving, for each of the subsets of the plurality of therapy parameter sets, feedback from the patient indicating whether the subset of the plurality of therapy parameter sets treated the condition of the patient; and means for selecting, based on the feedback from the patient, at least one subset of the plurality of therapy parameter sets that treat the condition of the patient for defining subsequent delivery of electrical stimulation therapy to the patient.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
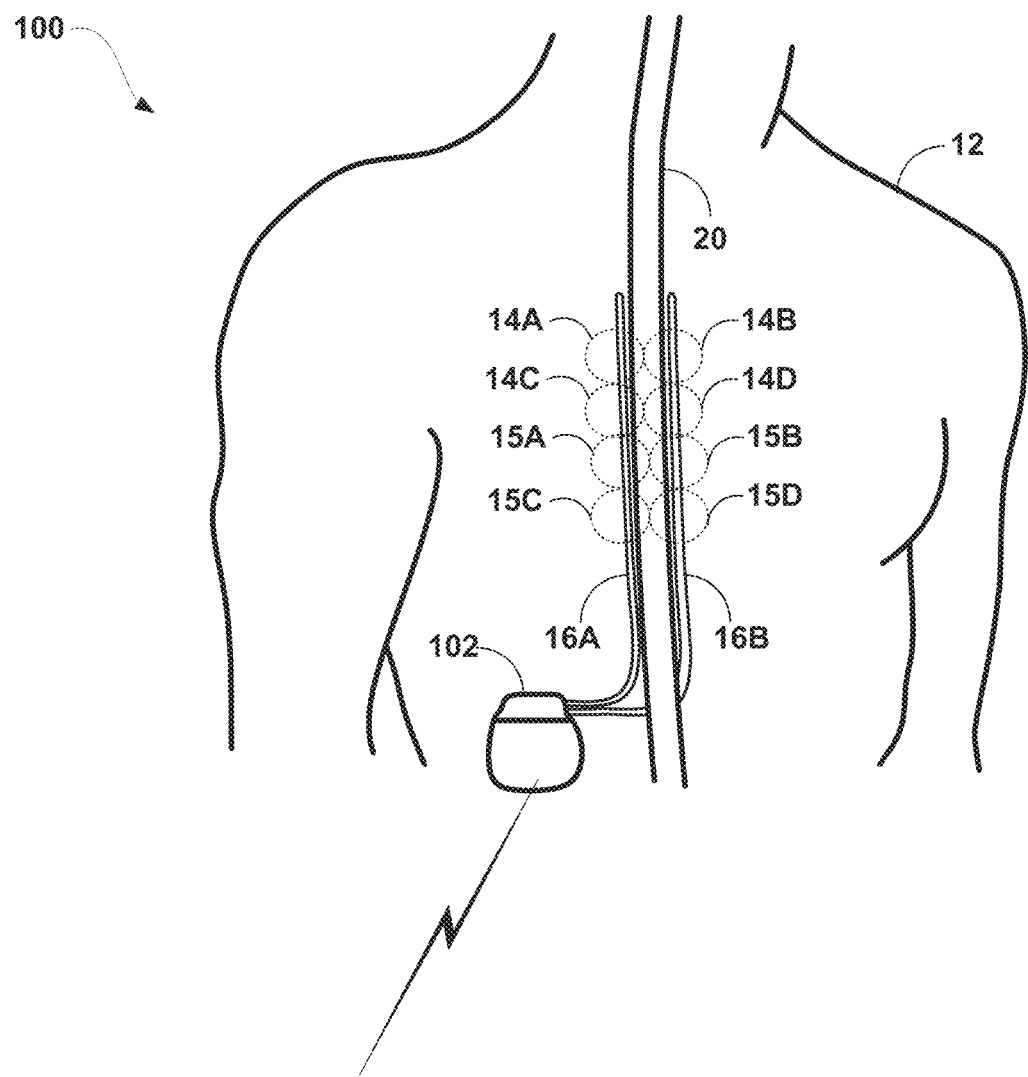
FIG. 1 is a conceptual diagram illustrating an example system that includes a medical device programmer and an implantable medical device (IMD) configured to deliver electrical stimulation therapy to a patient.

An implantable medical device may deliver electrical stimulation therapy to treat a condition of a patient. High-frequency electrical stimulation (e.g., electrical stimulation having pulses of a frequency greater than or equal to 1,000 Hertz) can be effective at treating conditions such as pain during SCS. For example, when treating chronic pain in a patient, low-frequency electrical stimulation may induce paresthesia in the patient, which masks the sensation of pain, but the sensation of paresthesia itself may be uncomfortable to the patient. In contrast, high-frequency electrical stimulation may suppress pain in the patient without substantially producing paresthesia (e.g., without causing perceptible sensations of paresthesia in the patient). Furthermore, increasing the frequency of the electrical stimulation therapy beyond 1,000 Hertz, or some other similar threshold for a patient) may not provide any additional benefit in treating the condition of the patient and also may not be perceived any differently by the patient.

The efficacy of the electrical stimulation may be related to one or more parameters of the electrical stimulation, such as the frequency of the electrical stimulation, as described above, as well as the pulse width of the electrical stimulation, one of current amplitude or voltage amplitude of the electrical stimulation, a combination of electrodes, etc. Furthermore, the efficacy of the electrical stimulation therapy may depend on the placement of individual electrodes disposed along one or more leads of the IMD relative to a spinal cord of the patient. Therefore, after a procedure in which a lead and/or an IMD is implanted within a patient, a clinician may test, in a clinic or an outpatient setting, electrical stimulation therapy defined by various electrical stimulation therapy parameter sets to determine an electrical stimulation therapy that effectively treats a condition of the patient. This period may be referred to as a trial period. As one example, the clinician may test various combinations of electrodes and different electrical stimulation therapy parameters, etc., to determine an electrical stimulation therapy that effectively suppresses one or more symptoms of a disease of the patient, such as chronic pain. In one example, such an outpatient evaluation may occur during an evaluation trial of about 10 days. However, during this trial, the patient may require several days to demonstrate a response to any particular electrical stimulation therapy program, such as paresthesia, pain relief, or the suppression of the one or more symptoms of the disease. Therefore, if the clinician were to test only a single electrical stimulation therapy at a time (e.g., a single electrode combination and location of the electrical stimulation therapy), he or she would be unable to test more than two or three different electrical stimulation therapy programs before the outpatient evaluation ends. Since there are likely many more options for therapy, the clinician may not have enough time to identify an electrical stimulation therapy program that effectively treats the condition of the patient. For example, in this limited trial period, the clinician may be unable to try all possible electrode combinations (e.g., deliver electrical stimulation to all possible tissue areas of the patient) to determine if an electrical stimulation program exists that is effective in treating the condition of the patient. Thus, upon individually testing only a few high-frequency electrical stimulation therapy programs that do not result in effective treatment of the condition of the patient, the clinician may need to choose an alternative therapy that may be less effective or determine that the patient is not a candidate for electrical stimulation therapy.

As described herein, a medical system is configured to deliver, via a plurality of electrode combinations of electrodes disposed along a lead of an IMD, a plurality of electrical stimulation therapy programs to the patient. In some examples, the IMD delivers each of the plurality of electrical stimulation therapy programs on a time-interleaved basis with one another, while in other examples, the IMD delivers each of the plurality of electrical stimulation therapy programs substantially simultaneously. In some examples where each of the plurality of electrical stimulation therapy programs on a time-interleaved basis with one another, each electrical stimulation therapy program may comprise a single electrical stimulation pulse. In either simultaneous deliver or time-interleaved delivery, the patient may perceive the effects of the plurality of electrical stimulation therapy programs at the same time. Furthermore, such electrical stimulation is delivered to a plurality of target tissue areas over a large portion of the spinal cord of the patient. By ensuring maximal coverage of the spinal cord, the clinician may quickly determine (e.g., within a trial period such as a trial period of about 3 days) whether the electrical stimulation therapy is capable of treating the condition of the patient. In this fashion, the techniques of the disclosure may allow for the rapid determination of whether electrical stimulation therapy is effective for treating a condition of patient. Furthermore, after determining whether the electrical stimulation is effective for treating the condition of the patient, the system may iteratively deliver electrical stimulation via subsets of electrodes to subsets of target tissue areas. In this fashion, the system may determine a primary set of electrodes that delivers electrical stimulation therapy to a tissue area smaller than the collective plurality of target tissue areas of the spinal cord of the patient while maintaining effective therapy. This reduction in electrodes, or therapy parameter sets, may allow the IMD to conserve energy by delivering electrical stimulation only via the primary set of electrodes to this smaller tissue area. This primary set of electrodes may be from one or more of the electrical stimulation therapy parameter sets tested with the plurality of electrical stimulation therapy parameter sets. Such techniques may reduce the power usage required to deliver the electrical stimulation over time while maintaining the desired therapy initially provided by delivery of the electrical stimulation therapy to the plurality of target tissue areas.

FIG. 1 is a conceptual diagram illustrating example system 100 that includes medical device programmer 104 and implantable medical device (IMD) 102 configured to deliver electrical stimulation therapy to patient 12. In the example shown in FIG. 1, IMD 102 is configured to deliver SCS therapy. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 102, leads 16A, 16B, and external programmer 104 shown in conjunction with a patient 12, who is ordinarily a human patient. In the example of FIG. 1, IMD 102 is an implantable electrical stimulator that is configured to generate and deliver electrical stimulation therapy to patient 12 via electrodes of leads 16A, 16B, e.g., to treat symptoms of a condition such as relief from chronic pain or other symptoms. IMD 102 may be a chronic electrical stimulator that remains implanted within patient 12 for weeks, months, or even years. In other examples, IMD 102 may be a temporary, or trial, stimulator used to screen or evaluate the efficacy of electrical stimulation for chronic therapy. In one example, IMD 102 is implanted within patient 12, while in another example, IMD 102 is an external device coupled to percutaneously implanted leads. In some examples, IMD uses one or more leads, while in other examples, IMD 102 is leadless. In some examples, leads 16A, 16B may be percutaneous leads for trial stimulation, chronic implanted leads, or include a display chronic implanted portion that carries the electrodes coupled to a lead extension that remains implanted within the patient and coupled to an implanted IMD 102 or coupled to a percutaneous lead extension that is coupled to an external IMD 102. In this manner, leads 16A, 16B may be used during a trial process with an external IMD and retained for use later with an implanted IMD.

IMD 102 may be constructed of any polymer, metal, or composite material sufficient to house the components of IMD 102 (e.g., components illustrated in FIG. 2) within patient 12. In this example, IMD 102 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 102 may be implanted within other suitable sites within patient 12, which may depend, for example, on the target site within patient 12 for the delivery of electrical stimulation therapy. The outer housing of IMD 102 may be configured to provide a hermetic seal for components, such as a rechargeable or non-rechargeable power source. In addition, in some examples, the outer housing of IMD 102 may be selected from a material that facilitates receiving energy to charge the rechargeable power source.

Electrical stimulation energy, which may be constant current or constant voltage based pulses, for example, is delivered from IMD 102 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 102. The electrodes may transfer electrical stimulation generated by an electrical stimulation generator in IMD 102 to tissue of patient 12. Although leads 16 may each be a single lead, lead 16 may include a lead extension or other segments that may aid in implantation or positioning of lead 16. In some other examples, IMD 102 may be a leadless stimulator with one or more arrays of electrodes arranged on a housing of the stimulator rather than leads that extend from the housing. In addition, in some other examples, system 100 may include one lead or more than two leads, each coupled to IMD 102 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

Electrical stimulation therapy is defined by a set of therapy parameters (e.g., a set of electrical stimulation parameters) that may also be referred to as a therapy program. The set of electrical stimulation parameters define delivery of stimulation therapy by IMD 102 through the electrodes of leads 16. The electrical stimulation parameters may include information identifying which electrodes have been selected for delivery of stimulation, the polarities of the selected electrodes, i.e., the electrode combination for the program, and voltage or current amplitude, pulse rate, and pulse width of electrical pulses delivered by the electrodes. Delivery of stimulation pulses will be described for purposes of illustration, but the electrical stimulation parameters may define other signals such as sine waves, triangle waves, square waves, or other types of electrical signals.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 102 to monitor one or more parameters of patient 12. The one or more sensors may be provided in addition to, or in place of, therapy delivery by lead 16.

IMD 102 is configured to deliver electrical stimulation therapy to patient 12 via selected combinations of electrodes carried by one or both of leads 16, alone or in combination with an electrode carried by or defined by an outer housing of IMD 102. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 20 in via any suitable region, such as the thoracic, cervical, or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy that treats a condition of the patient 12.

IMD 102 is configured to generate and deliver electrical stimulation therapy to a target stimulation site within patient 12 via the electrodes of leads 16 to patient 12 according to one or more therapy programs. A therapy program defines values for one or more electrical parameters that define an aspect of the therapy delivered by IMD 102 according to that program defining the electrical parameter values. For example, a therapy program that defines delivery of stimulation by IMD 102 in the form of pulses may define values for voltage or current pulse amplitude, pulse width, and pulse rate for stimulation pulses delivered by IMD 102.

Moreover, in some examples, IMD 102 delivers electrical stimulation therapy to patient 12 according to multiple therapy programs, which may be stored as a therapy program group. For example, as described below, in some examples, IMD 102 may deliver different pulses of electrical stimulation signal via respective electrode combinations, and each of the electrode combinations may be associated with a respective therapy program. The therapy programs may be stored as a group, such that when IMD 102 generates and delivers electrical stimulation therapy via a selected group, IMD 102 delivers electrical stimulation signal via two or more therapy programs. IMD 102 may be configured to deliver electrical stimulation defined by two or more therapy programs simultaneously or on a time-interleaved basis.

In some examples, IMD 102 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recovery signal" or a "charge balancing signal" and may have a polarity opposite to that of the electrical stimulation signal generated and delivered by IMD 102. While recharge pulses are primarily referred to herein, in other examples, a recharge signal can have any suitable waveform.

A user, such as a clinician or patient 12, may interact with a user interface of an external programmer 104 to program IMD 102. Programming of IMD 102 may refer generally to the generation and transfer of commands, programs, or other information to control the operation of IMD 102. In this manner, IMD 102 may receive the transferred commands and programs from programmer 104 to control stimulation therapy. For example, external programmer 104 may transmit therapy programs, stimulation parameter adjustments, therapy program selections, therapy program group selections, user input, or other information to control the operation of IMD 102, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 102, whereas a patient programmer may support adjustment and selection of such programs by a patient during ordinary use. In other examples, external programmer 104 may be included, or part of, an external charging device that recharges a power source of IMD 102. In this manner, a user may program and charge IMD 102 using one device, or multiple devices.

As described herein, information may be transmitted between external programmer 104 and IMD 102. Therefore, IMD 102 and programmer 104 may communicate via wireless communication using any techniques known in the art. Examples of communication techniques may include, for example, radiofrequency (RF) telemetry and inductive coupling, but other techniques are also contemplated. In some examples, programmer 104 may include a communication head that may be placed proximate to the patient's body near the IMD 102 implant site in order to improve the quality or security of communication between IMD 102 and programmer 104. Communication between programmer 104 and IMD 102 may occur during power transmission or separate from power transmission.

In some examples, IMD 102 delivers a recharge signal after delivery of multiple pulses of an electrical stimulation signal, which may be defined by one therapy program or by multiple therapy programs. Thus, rather than charge balancing on a pulse-by-pulse basis (e.g., delivering one recharge pulse after each electrical stimulation pulse), in some examples, IMD 102 delivers one or more recharge pulses after delivery of two or more electrical stimulation pulses. In some examples, IMD 102 delivers an electrical stimulation signal to patient 12 according to multiple therapy programs by at least interleaving pulses of two or more therapy programs, the pulses having a first polarity. In some of these examples, IMD 102 may wait to deliver one or more recharge pulses until after one or more pulses of each of the therapy programs are delivered, each recharge pulse having a second polarity opposite to the first polarity. Thus, in some examples, IMD 102 may not deliver any recharge signals between therapy programs, but, rather, may withhold the delivery of one or more recharge signals until after IMD 102 delivers a plurality of pulses according to two or more therapy programs.

As described below, IMD 102, in response to commands from external programmer 104, may be configured to deliver electrical stimulation therapy according to a plurality of electrical stimulation therapy parameter sets to a plurality of respective target tissue areas of the spinal column 20 of patient 12 via electrodes (not depicted) on leads 16. IMD 102 may be configured to deliver the electrical stimulation therapy according to the plurality of electrical stimulation therapy parameter sets simultaneously (e.g., where a pulse from one stimulation therapy is delivered simultaneous with a pulse from another stimulation therapy) or time-interleaved (e.g., pulses from each stimulation therapy are alternated in time). In some examples, each electrical stimulation therapy program comprises electrical stimulation pulses at a high frequency, e.g., a frequency of greater than 1,000 Hertz, a frequency of greater than approximately 1.2 kHz, a frequency of greater than 1.5 kHz, or a frequency between 5 and 10 kHz.

High-frequency stimulation may be effective in alleviating or reducing chronic pain while avoiding the need to cause paresthesia in patients. However, as the frequency of the electrical stimulation increases beyond a certain frequency threshold, such as 1,000 Hertz for example, a patient may not notice any difference with higher frequencies or derive any further therapeutic benefit, such as reduction in the severity of one or more symptoms of a disease of the patient. Therefore, IMD 102 may deliver electrical stimulation from different electrode combinations (e.g., effecting different tissue sites using multiple programs) without tissues within the zones of stimulation of the multiple programs and subject to pulses from electrical stimulation therapy according to different electrical stimulation therapy parameter sets perceiving any differences in stimulation. In some examples, the zones of stimulation from electrical stimulation therapy according to a plurality of electrical stimulation therapy parameter sets delivered by each set of electrodes do not overlap with one another. In other examples, when electrical stimulation therapy according to the electrical stimulation therapy parameter sets are delivered on a time-interleaved basis with one another and the respective zones of stimulation reach a common tissue area, the tissue affected by both zones of stimulation from the plurality of electrical stimulation pulses delivered by each set of electrodes perceives an effective pulse rate, or frequency of a combined electrical stimulation at that common target tissue site. In some examples, the combined or effective pulse rate has a uniform distribution of pulses such that the combined pulse burst has a uniform frequency. In other examples, the combined or effective pulse rate has a non-uniform distribution of pulses (e.g., the pulses have differing inter-pulse intervals and/or different pulse widths within a certain period of time). Thus, delivering electrical stimulation therapy according to a plurality of electrical stimulation therapy parameter sets on a time-interleaved basis with one another may cause, at the intersection of each electric field of each respective electrical therapy stimulation therapy, specific areas of high frequency therapy that are not necessarily located immediately next to the electrodes. This time-interleaved higher frequency stimulation delivery facilitates more flexibility in targeting the higher frequency to the targeted location that may not be immediately near an electrode and can reduce side effects if providing high frequency stimulation is not desired in close proximity to the electrodes. Further description of the use of interleaving a plurality of lower-frequency electrical stimulation therapy programs to deliver an effective higher-frequency electrical stimulation program to a target tissue area are described in U.S. patent application Ser. No. 15/623,141 to Torgerson, entitled "DELIVERY OF INDEPENDENT INTERLEAVED PROGRAMS TO PRODUCE HIGHER-FREQUENCY ELECTRICAL STIMULATION THERAPY" and filed on Jul. 14, 2017, the entire content of which is incorporated by reference herein.

In some examples, IMD 102 is configured to generate and deliver electrical stimulation therapy according to a plurality of electrical stimulation therapy parameter sets to patient 12 via a plurality of electrodes, e.g., of leads 16 and/or a housing of IMD 102, each electrical stimulation therapy parameter set of the plurality of electrical stimulation therapy parameter sets delivered via two or more electrodes of the plurality of electrodes. Each electrical stimulation therapy signal may have a frequency of greater than approximately 1000 Hertz in some examples, greater than approximately 1,200 Hertz in some examples, greater than 1,500 Hertz in other examples, greater than 5,000 Hertz in other examples, or greater than 10,000 Hertz in still other examples. Additionally, each electrical stimulation therapy signal may have a frequency of less than approximately 20,000 Hertz in some examples, less than 10,000 Hertz in other examples, or less than 5,000 Hertz in still other examples.

In some examples, each electrical stimulation therapy signal may have a frequency greater than approximately 900 Hertz and less than approximately 1,500 Hertz. In other examples, each electrical stimulation therapy signal may have a frequency may be greater than approximately 1,200 Hertz and less than approximately 20,000 Hertz, or greater than approximately 1,200 Hertz and less than approximately 5,000 Hertz in other examples. In some examples, each electrical stimulation therapy has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In some examples, the amplitude and pulse width of the electrical stimulation signal are selected such that a stimulation intensity level of the electrical stimulation signal is less than a perception or paresthesia threshold intensity level for patient 12. Stimulation delivered at an intensity that is less than a perception or paresthesia threshold intensity level for patient 12 may be referred to as sub-threshold stimulation. The perception threshold is the lowest level of electrical stimulation that is sufficient for the patient to perceive that the IMD is delivering electrical stimulation. The paresthesia threshold is the lowest level of electrical stimulation that causes paresthesia in the patient. Paresthesia may cause discomfort in the patient, and is sometimes described as a "pins and needles" sensation, but that discomfort or tingling may mask and be more tolerable than pain otherwise felt by the patient. A clinician may select one or more parameters of the electrical stimulation therapy, and titrate the one or more parameters until the electrical stimulation therapy is less than a perception or paresthesia threshold intensity level for patient 12. In one example, the electrical stimulation signal has a current amplitude in a range of 0.1 microamps to 100 milliamps. In another example, the amplitude may be selected to be in a range of about 0.1 milliamps to about 25 milliamps, such as in a range of about 0.5 milliamps to about 5 milliamps. In another example, the electrical stimulation signal has a voltage amplitude in a range of 10 millivolts to 14 Volts. In another example, the electrical stimulation signal has a voltage amplitude in a range of 50 millivolts to 14 Volts, such as in a range of about 500 millivolts to about 5 Volts.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

In some examples, IMD 102 delivers the pulses of the electrical stimulation signal via a plurality of different electrode combinations. For example, IMD 102 may alternate delivery of pulses between two different electrode combinations (e.g., different electrical stimulation therapy parameter sets), or may otherwise interleave the pulses using two or more electrode combinations in any suitable order. In some examples, IMD 102 may deliver time-interleaved pulses via two, three, four or more electrode combinations. IMD 102 may alternate between delivery of a single pulse on each of two or more electrode combinations over a series of time intervals. In some examples, zones of stimulation generated by each electrode combination do not overlap such that each target tissue site receives electrical stimulation from only a single respective electrode combination. In other examples, zones of stimulation generated by each electrode combination overlap with zones of stimulation generated by each other electrode combination so as to create a combined zones of stimulation at a target tissue site. In other examples, the zones of stimulation generated by each electrode combination overlap with zones of stimulation generated by each other electrode combination. As an illustration, IMD 102 may deliver a first pulse in a first time interval via a first electrode combination, a second pulse in a second time interval via a second electrode combination, a third pulse in a third time interval via a third electrode combination, and a fourth pulse in a fourth time interval via a fourth electrode combination, and repeat this process, e.g., on a periodic basis. In other examples, IMD 102 may alternate between delivery of multiple pulses between two or more different electrode combinations over successive time intervals. As an illustration, IMD 102 may deliver a two or more first pulses in a first time interval via a first electrode combination, two or more second pulses in a second time interval via a second electrode combination, two or more third pulses in a third time interval via a third electrode combination, and two or more fourth pulses in a fourth time interval via a fourth electrode combination, and repeat this process, e.g., on a periodic basis. In one example, each electrode combination comprises one electrode functioning as an anode and another electrode functioning as a cathode, and these electrodes are unique to the electrode combination, i.e., the electrodes used for delivery of stimulation pulses in one electrode combinations are not used in any of the other electrode combinations. In another example, each electrode combination comprises a plurality of electrodes functioning as anodes in conjunction with a cathode and/or a plurality of electrodes functioning as cathodes in conjunction with an anode, and each of these pluralities of electrodes is unique to the electrode combination.

In some examples where IMD 102 delivers electrical stimulation therapy according to the different electrical stimulation therapy parameter sets on a time-interleaved basis with one another, IMD 102 may cease delivery of a first electrical stimulation therapy for a period of time prior to switching to the next electrical stimulation therapy. In other words, IMD 102 may deliver a first electrical stimulation therapy and cease delivery of all electrical stimulation therapy for a period of time. After the period of time has elapsed, IMD 102 may deliver a second electrical stimulation therapy and then cease delivery of all electrical stimulation therapy for the period of time. After the period of time has elapsed again, IMD 102 may deliver a third electrical stimulation therapy, etc. By ceasing delivery of electrical stimulation therapy between different electrical stimulation therapy parameter sets, IMD 102 may avoid overstimulating the target tissue sites of patient 12. Furthermore, by ceasing delivery of electrical stimulation therapy between different electrical stimulation therapy parameter sets, IMD 102 may ensure that any effects on patient 12 of a second electrical stimulation therapy are due to the second electrical stimulation therapy, and not due to residual energy from a first electrical stimulation therapy. In some examples, IMD 102 may cease delivery of all stimulation during the transition between the different electrical stimulation therapy parameter sets for a period of time of about 500 milliseconds. In other examples, the period of time is less than about 500 milliseconds.

In a typical lead implantation procedure, the clinician may insert one or more electrode leads 16 along spinal cord 20 of patient 12. The clinician may attempt to place leads 16 such that at least one electrode of lead 16A and at least one electrode of lead 16B are on opposite sides of spinal cord 20. However, it is presently not well understood where, along spinal cord 20, an optimal location for delivery of electrical stimulation may lie such that the electrical stimulation exhibits efficacy in treating a condition of patient 12. For example, such a location may differ from patient to patient and may also depend on the proximity of individual electrodes along leads 16 to one another and on the individual electrical characteristics of each of the electrodes.

After implantation of the leads, the clinician may test the placement of electrodes. In some examples, the clinician connects the leads to an external medical device. The clinician may test various electrical stimulation therapy parameter sets to determine an electrical stimulation therapy that effectively treats a condition of patient 12. For example, the clinician may test various combinations of electrodes and different electrical stimulation therapy parameters, etc. to determine an electrical stimulation therapy that effectively suppresses one or more symptoms of the disease of patient 12, such as chronic pain. Such a trial outpatient evaluation may occur over about 10 days. However, in some examples, patient 12 may require several days to demonstrate a response to the electrical stimulation, such as paresthesia, pain relief, or the suppression of the one or more symptoms of the disease. Thus, if the clinician were to test only a single electrical stimulation therapy parameter set at a time, he or she would be unable to test more than two or three different electrical stimulation therapy parameter sets before the time for the outpatient evaluation ends.

In accordance with the techniques of the disclosure, medical system 100 is configured to deliver, via a plurality of electrode combinations of electrodes disposed along lead 16 of a medical device, such as IMD 102, a plurality of electrical stimulation therapy programs to patient 12. In some examples, the medical device delivers each of the plurality of electrical stimulation therapy programs on a time-interleaved basis with one another, while in other examples, the medical device delivers each of the plurality of electrical stimulation therapy programs substantially simultaneously. Furthermore, such electrical stimulation is delivered via a plurality of electrodes to a plurality of target tissue areas over a large portion of spinal cord 20 of patient 12. By ensuring maximal coverage of spinal cord 20, the clinician may quickly determine (e.g., within one test period of about 3 days) whether the electrical stimulation therapy is capable of treating a condition of patient 12. In this fashion, the techniques of the disclosure may allow for the rapid determination of whether electrical stimulation therapy is effective for treating a condition of patient 12.

After determining whether the electrical stimulation is effective for treating a condition of patient 12, the clinician may implant an implantable medical device, such as IMD 102, within patient 12 and connects the leads to the implantable medical device. However, in some examples, the above determination of whether the electrical stimulation is effective for treating the condition of patient 12 is performed after implanting IMD 102. At this time, the clinician may attempt to remove one or more electrodes that deliver the electrical stimulation therapy so as to reduce power consumption of IMD 102. In some examples, this occurs in an outpatient setting. As one example, IMD 102 iteratively delivers electrical stimulation via subsets of the plurality of electrodes to subsets of the plurality of target tissue areas. In this fashion, the techniques of the disclosure may determine a primary set of electrodes 116, 118 that delivers electrical stimulation therapy to a tissue area smaller than the collective plurality of target tissue areas while maintaining effective therapy. In turn, IMD 102 may conserve energy by delivering electrical stimulation via the primary set of electrodes to this smaller tissue area. Such techniques may reduce the power usage required to deliver the electrical stimulation over time while maintaining the desired therapy initially provided by delivery of the electrical stimulation therapy to the plurality of target tissue areas.

In one example of the techniques of the disclosure, after the clinician implants the leads, the clinician selects a first electrode combination of a medical device, such as an external medical device or an implantable medical device such as IMD 102, that is configured to deliver electrical stimulation via the first electrode combination to a first plurality of target tissue sites along spinal cord 20 of patient 12. The medical device controls delivery of the electrical stimulation to the first plurality of target tissue sites along spinal cord 20 of patient 12. In one example, the clinician selects a first set of electrodes configured to deliver a first electrical pulse train having a frequency of approximately 1,000 Hertz to a set of four tissue sites along the T9-T10 disc space of patient 12 (e.g., tissue sites 14A, 14B, 14C, and 14D). If patient 12 does not experience pain relief after several days, the clinician selects a second electrode combination configured to deliver electrical stimulation to a second plurality of target tissue sites along the spinal cord of patient 12 (e.g., tissue sites 15A, 15B, 15C, and 15D). In this example, the clinician may select a second set of electrodes configured to deliver a second electrical pulse train having a frequency of approximately 1,000 Hertz to the set of four tissue sites 15A, 15B, 15C, and 15D along the T9-T10 disc space of patient 12. In this example, upon determining that the second electrical pulse train delivered to the set of four tissue sites 15A, 15B, 15C, and 15D treats a condition of patient 12, the clinician may select the second set of electrodes for subsequent delivery of electrical stimulation therapy to patient 12.

In some examples, after the clinician has determined that electrical stimulation delivered to a plurality of tissue sites results in treatment of the patient's condition, the clinician disconnects an external medical device from the leads implanted within patient 12, implants an implantable medical device, such as IMD 102, within patient 12, and connects the leads to IMD 102. Further, the clinician may attempt to reduce the number of electrodes, or number of programs, for subsequent therapy while maintaining effective treatment. This reduction in electrodes and stimulation coverage area may be possible for high-frequency electrical stimulation since the therapeutic effect may be generated only from high-frequency electrical stimulation delivered to a specific tissue site while high frequency electrical stimulation delivered to extraneous tissue sites may not affect the therapeutic effect. Furthermore, the system may iteratively test the efficacy of each individual electrode combination of the electrodes used to deliver the plurality of electrical stimulation therapy programs by removing one or more of the 1,000 Hertz programs. As one example, the clinician may select a third set of electrodes configured to deliver a third electrical pulse train having a frequency of approximately 1,000 Hertz to a set of two tissue sites 15A and 15B along the T9-T10 disc space of patient 12. If patient 12 does not experience pain relief after several days, the clinician selects a fourth electrode combination configured to deliver a fourth electrical pulse train having a frequency of approximately 1,000 Hertz to a set of two tissue sites 15C and 15D along the T9-T10 disc space of patient 12. In this example, upon determining that the fourth electrical pulse train delivered to the set of two tissue sites 15C and 15D treats a condition of patient 12, the clinician may select the second set of electrodes for subsequent delivery of therapy to patient 12.

In another example, instead of removing electrodes to try and reduce the area (or tissue sites) of the effective stimulation therapy, the system may isolate electrode combinations or individual programs to evaluate small tissue areas and work larger until the therapy can be maintained. For example, the clinician may select a fifth set of electrodes configured to deliver a fifth electrical pulse train having a frequency of approximately 1,000 Hertz to only tissue site 15C along the T9-T10 disc space of patient 12. If patient 12 does not experience pain relief after several days, the clinician selects a sixth electrode combination configured to deliver a sixth electrical pulse train having a frequency of approximately 1,000 Hertz to only tissue site 15D along the T9-T10 disc space of patient 12. In this example, upon determining that the sixth electrical pulse train delivered to tissue site 15D treats a condition of patient 12, the clinician may select the sixth set of electrodes for subsequent delivery of therapy to patient 12.

As yet another example where the clinician iteratively tests the efficacy of each individual electrode combination by removing some of the 1,000 Hertz programs, the clinician selects a first combination of electrodes configured to deliver a first electrical pulse train having a frequency of approximately 1,000 Hertz to a set of four tissue sites along the T9-T10 disc space of patient 12 (e.g., tissue sites 14A, 14B, 14C, and 14D). If, after several days, patient 12 does not experience pain relief, the clinician may select a second combination of electrodes configured to deliver a first electrical pulse train having a frequency of approximately 1,000 Hertz to a set of four tissue sites along the T9-T10 disc space of patient 12 (e.g., tissue sites 15A, 15B, 15C, and 15D). Alternatively, if, after several days, patient 12 experiences pain relief, the clinician removes one subset of electrodes (e.g., those configured to provide therapy to tissue site 14A) and continues delivering electrical stimulation to tissue sites 14B, 14C, and 14D. If, after another several days, patient 12 continues experiencing pain relief, the clinician removes another subset of electrodes (e.g., those configured to provide therapy to tissue site 14B) and continues delivering electrical stimulation to tissue sites 14C and 14D. If patient 12 experiences a return of pain, the clinician may restore the removed subset of electrodes (e.g., those configured to provide therapy to tissue site 14B), remove a different subset of electrodes (e.g., those configured to provide therapy to tissue site 14C) and continue iteratively testing delivery of electrical stimulation to tissue sites 14B and 14D. The clinician may continue such iterative testing of electrode combinations until the clinician determines a minimum number of electrode combinations that effectively treat the condition of patient 12.

In other examples, after a plurality of electrical stimulation therapy parameter sets are determined to be effective in treating the patient, the system may remove of one or more electrodes (e.g., one or more electrical stimulation therapy parameter sets) according to a predetermined scheme (e.g., by removing electrode combinations in proximal or distal order along a lead) or by random selection. In one example, the clinician may continue to remove electrode combinations until every combination of electrodes has been tested individually for efficacy. In another example, the clinician may continue to remove electrode combinations until the clinician determines a minimum number of electrode combinations required to provide electrical stimulation therapy treats a condition of patient 12, such as suppressing pain.

In some examples, the iterative testing of combinations of electrodes may be performed by the clinician in an outpatient setting after completion of an implantation procedure of IMD 102. In other examples, IMD 102 may iteratively test combinations of electrodes on a periodic basis, e.g., monthly, bimonthly, or yearly. In the examples described above, the terms evaluation period, test period, and trial period are used interchangeably and refer to the time period that the IMD iteratively tests combinations of electrodes. Such a test period may last for about one to two weeks or less. Further, upon determining a primary set of electrodes that effectively treats a condition of patient 12, as described above, IMD 102 delivers electrical stimulation to patient 12 over a chronic period. As used throughout, the chronic period refers to the time period that IMD 102 delivers electrical stimulation therapy to patient 112 to treat the condition of patient 112. The chronic time period may be the operable lifetime of IMD 102. Typically, the test period is much shorter than the chronic period and used for evaluation of therapy.

Thus, by removing electrodes or programs that do not contribute to the treatment, the techniques of the disclosure may reduce the number of electrodes delivering electrical stimulation, and thereby reduce the power consumed by IMD 102 when delivering therapy. In other words, removing electrodes or programs may reduce the area of stimulation and current used by the IMD 102. By reducing the power consumption of IMD 102, the techniques of the disclosure may increase the time that IMD 102 may function without recharging, in the case of a rechargeable IMD, or increase the operative life of a non-rechargeable IMD. In addition, the techniques of the disclose may increase the number of tissue sites (or area of tissue) that a clinician may test in a limited amount of time, thereby increasing the chance of identifying electrical stimulation effective in alleviating symptoms of pain of patient 12. Then, after stimulation is deemed to be effective, the system can work on identifying electrode combinations with fewer electrodes to reduce the power consumption of IMD 102 while maintaining therapy efficacy.

Although IMD 102 is generally described herein, techniques of this disclosure may also be applicable to external or partially external medical device in other examples. For example, IMD 102 may instead be configured as an external medical device coupled to one or more percutaneous medical leads. The external medical device may be a chronic, temporary, or trial electrical stimulator. In addition, an external electrical stimulator may be used in addition to one or more IMDs 102 to deliver electrical stimulation described herein.

Figure 2:
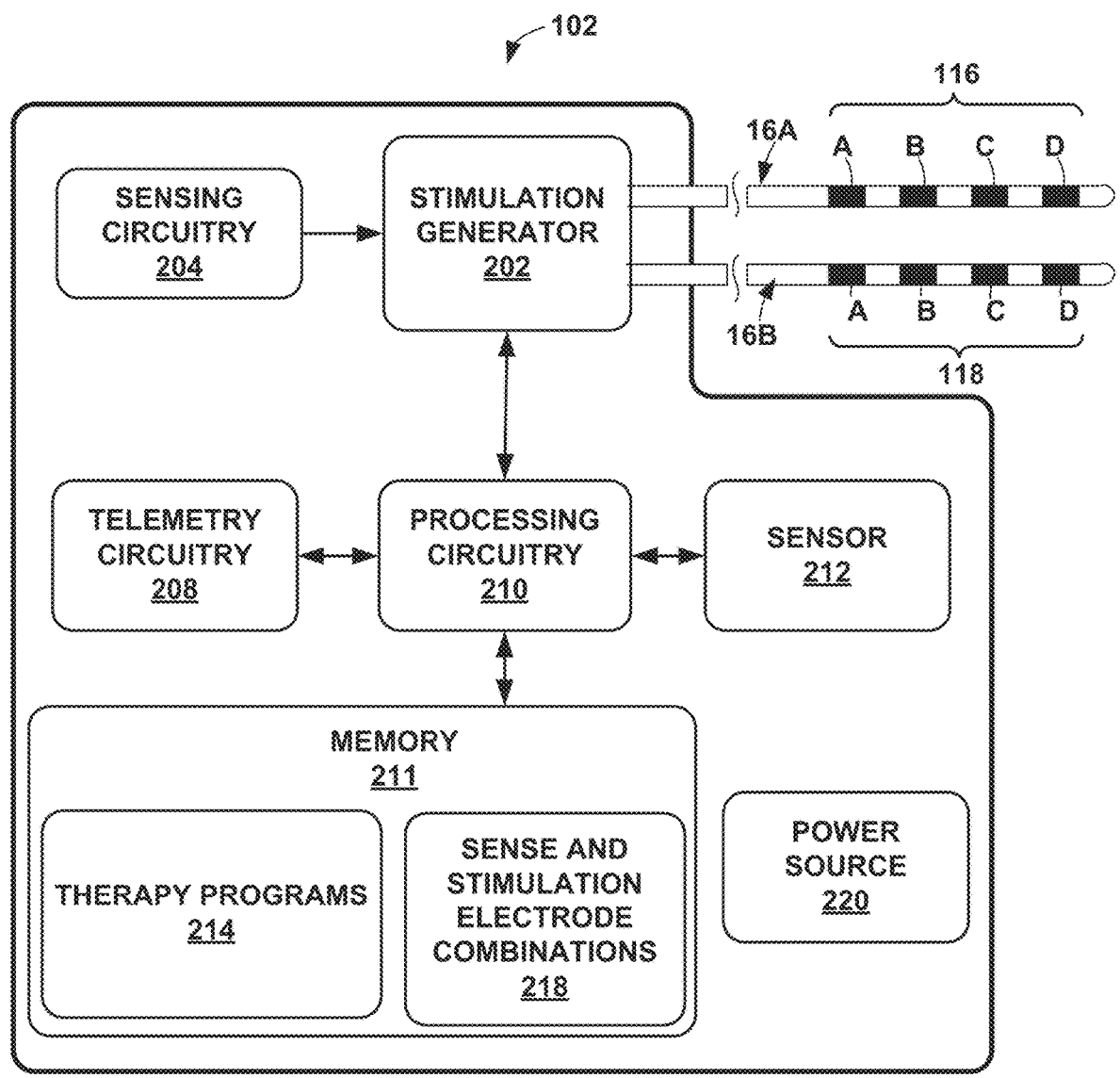
FIG. 2 is a block diagram of the example IMD of FIG. 1.

FIG. 2 is a block diagram of the example IMD 102 of FIG. 1. In the example shown in FIG. 2, IMD 102 includes processing circuitry 210, memory 211, stimulation generator 202, sensing circuitry 204, telemetry circuitry 208, sensor 212, and power source 220. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping (e.g., simultaneous) or non-overlapping (e.g., time-interleaved) basis.

The techniques of the disclosure are described in some examples as interleaving stimulation pulses on a non-overlapping (time-interleaved) basis. However, in some examples, the techniques of the disclosure may allow for interleaving stimulation pulses delivered via different sets of electrodes on an at least partially overlapping, or fully overlapping, basis. Overlapping of the recharge or recovery pulses of the different programs or electrode combinations may be useful because it may allow more time to discharge series capacitors on the electrodes. This may allow the system to operate more efficiently. For example, each of the plurality of electrical stimulation programs delivers therapy pulses on unique electrodes. However, during the time of the recovery pulse, each of the electrodes used in all of the electrical stimulation therapy programs are tied together on the IMD and connected to the body. This allows the series capacitors of the electrodes to simultaneously discharge to balance the therapy pulses. Such a system allows for recovery pulses having a lower amplitude than other systems, and therefore, such a system may disperse the energy more uniformly to the tissue of the patient instead of localizing it to the specific electrode combination.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls stimulation generator 202 to generate and apply the stimulation signals to selected combinations of electrodes 116, 118. In some examples, stimulation generator 202 includes switch circuitry that selectively transmits stimulation signals to selected conductors within leads 16, which, in turn, deliver the stimulation signals across selected electrodes 116, 118. Such switch circuitry ma y be a switch array, switch matrix, multiplexer, or any other type of switching circuitry configured to selectively couple stimulation energy to selected electrodes 116, 118 and to selectively sense bioelectrical neural signals of spinal cord 20 with selected electrodes 116, 118.

In other examples, however, stimulation generator 202 does not include switch circuitry. In these examples, stimulation generator 202 comprises a plurality of pairs of voltage sources, current sources, voltage sinks, or current sinks connected to each of electrodes 116, 118 such that each pair of electrodes has a unique signal generator. In other words, in these examples, each of electrodes 116, 118 is independently controlled via its own signal generator (e.g., via a combination of a regulated voltage source and sink or regulated current source and sink), as opposed to switching signals between electrodes 116, 118.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, switch circuitry of stimulation generator 202 may serve to time divide the output of stimulation generator 202 across different electrode combinations at different times to deliver multiple programs or channels of stimulation energy to patient 112. In another example, the stimulation generator 202 may control the independent sources or sinks on a time-interleaved bases.

Electrodes 116, 118 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. On one example, the electrodes may be electrically coupled to switch circuitry 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuitry 204 is incorporated into a common housing with stimulation generator 202 and processing circuitry 210 in FIG. 2, in other examples, sensing circuitry 204 may be in a separate housing from IMD 102 and may communicate with processing circuitry 210 via wired or wireless communication techniques. Example bioelectrical signals include, but are not limited to, a signal generated from local field potentials within one or more regions of spinal cord 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to the patient).

Telemetry circuitry 208 supports wireless communication between IMD 102 and an external programmer 104 or another computing device under the control of processing circuitry 210. Processing circuitry 210 of IMD 102 may receive, as updates to programs, values for various stimulation parameters such as amplitude and electrode combination, from programmer 104 via telemetry circuitry 208. The updates to the therapy programs may be stored within therapy programs 214 portion of memory 211. Telemetry circuitry 208 in IMD 102, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 102 with programmer 104. Accordingly, telemetry circuitry 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, telemetry circuitry 208 of IMD 102 receives commands from an external programmer 104. In response to these commands, processing circuitry 210 of IMD 102 delivers a plurality of electrical stimulation therapy programs to a plurality of target tissue areas of the spinal column 20 of patient 12 via electrodes 116, 118 of leads 16.

In some examples, IMD 102 is configured to generate and deliver electrical stimulation therapy to patient 12 via two or more pairs of electrodes, e.g., combinations of two or more of electrodes 116A-116D and 118A-118D, e.g., of leads 16 and/or a housing of IMD 102. In some examples, each individual pulse train delivered on the two or more pairs of electrodes has a frequency in a range of about 1000 Hertz to about 1500 Hertz, although frequencies lower and higher than this range may also be used. The amplitude and pulse width of the electrical stimulation signal are selected such that a stimulation intensity level of the electrical stimulation signal is less than a perception or paresthesia threshold intensity level for patient 12. For example, in a current-controlled implementation, the amplitude may be selected to be in a range of 0.1 microamps to 100 milliamps. In another example, the amplitude may be selected to be in a range of about 0.1 milliamps to about 25 milliamps, such as in a range of about 0.5 milliamps to about 5 milliamps. In another example, in a voltage-controlled implementation, the amplitude may be selected to be in a range of 10 millivolts to 14 Volts. In another example, the voltage amplitude may be selected to be in a range of about 50 millivolts to about 14 volts, such as in a range of about 500 millivolts to about 5 Volts.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

In some examples, IMD 102 delivers the pulses of the electrical stimulation signal via different electrode combinations of two or more of electrodes 116A-116D and 118A-118D and a housing of IMD 102. For example, IMD 102 may alternate delivery of pulses between two or more different electrode combinations, or may otherwise interleave the pulses using two or more electrode combinations in any suitable order. In one example, each electrode combination comprises at least one electrode functioning as an anode and at least one other electrode functioning as a cathode, and these electrodes are unique to the electrode combination in that the same electrodes are not used in other electrode combinations that are used to delivery time-interleaved stimulation pulses.

The electrical stimulation therapy signal may have a frequency of greater than approximately 1000 Hertz in some examples, greater than approximately 1,200 Hertz in some examples, greater than 1,500 Hertz in other examples, greater than 5,000 Hertz in other examples, or greater than 10,000 Hertz in still other examples. Additionally, the electrical stimulation therapy signal may have a frequency of less than approximately 20,000 Hertz in some examples, less than 10,000 Hertz in other examples, or less than 5,000 Hertz in still other examples. In some examples, the frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In another example, in response to telemetry circuitry 208 receiving commands from an external programmer 104, processing circuitry 210 of IMD 102 selects the target tissue area by selecting different electrode combinations of two or more of electrodes 116A-116D and 118A-118D and a housing of IMD 102 that share common anodes electrodes or cathode electrodes. For example, processing circuitry 210 of IMD 102 selects a first electrical stimulation therapy program delivered via a first electrode combination including anode electrode 116A and cathode electrode 118A, a second electrical stimulation therapy program delivered via a second electrode combination including anode electrode 116B and cathode electrode 118A, a third electrical stimulation therapy program delivered via a third electrode combination including anode electrode 116C and cathode electrode 118A, and a fourth electrical stimulation therapy program delivered via a fourth electrode combination having anode electrode 116D and cathode electrode 118A. In this example, the tissue proximate to the cathode electrode 118A may receive a pulse train signal that is a combination of the first, second, third, and fourth electrical stimulation therapy programs, while other tissues of patient 12 near anode electrodes 116A-116D may receive electrical stimulation due to only a single respective electrical stimulation therapy programs.

In another example, in response to telemetry circuitry 208 receiving commands from an external programmer 104, processing circuitry 210 of IMD 102 selects a plurality of electrode combinations, each combination having a plurality of unique anodes located down the spinal cord 20 and a plurality of common cathodes located proximate to the dorsal root of patient 12. In this example, for each target tissue area of the plurality of target tissue areas, processing circuitry 210 of IMD 102 selects an electrode combination. For example, for a first target tissue area, processing circuitry 201 selects a first electrical stimulation therapy program delivered via a first electrode combination (e.g., anode electrode 116A and cathode electrodes 118A-118D), for a second target tissue area, processing circuitry 2010 selects a second electrical stimulation therapy program delivered via a second electrode combination (e.g., anode electrode 116B and cathode electrodes 118A-118D), for a third target tissue area, processing circuitry 2010 selects a third electrical stimulation therapy program delivered via a third electrode combination (e.g., anode electrode 116C and cathode electrodes 118A-118D), and for a fourth target tissue area, processing circuitry 210 selects a fourth electrical stimulation therapy program delivered via a fourth electrode combination (e.g., anode electrode 116D and cathode electrodes 118A-118D). In this example, a central region of tissue area of patient 12 (e.g., the tissue near cathode electrodes 118A-118D) may receive electrical stimulation from each of the four electrode combinations 118A-118D, while other tissues of patient 12 (e.g., the tissue near anode electrodes 116A-116D) may receive only electrical stimulation from a single electrode combination. By delivering electrical stimulation according to a plurality of such electrical stimulation therapy parameter sets to a plurality of respective tissue sites 14A-14D and 15A-15D, IMD 102 may increase the likelihood that the dorsal root area of patient 12 receives electrical stimulation from at least one of the electrical stimulation therapy parameter sets. In this fashion, the techniques of the disclosure allow for quickly determining whether electrical stimulation therapy may treat a condition of patient 12 without spending time determining which electrodes may be correctly positioned so as to stimulate desired target tissue regions of spinal cord 20. Although some tissues may be subject to the zones of stimulation generated by multiple electrode combinations, these overlapping stimulation fields at high frequency pulses may not induce any different tissue response as compared to being subject to only one stimulation field. For example, the response from tissue receiving pulses at 1,000 Hz from a single electrode combination may be similar to the response from the same tissue receiving pulses at a collective 4,000 Hz from four different time-interleaved electrode combinations at 1,000 Hz each. Therefore, the system may be able to trial, or evaluate, electrical stimulation efficacy from a plurality of electrode combinations at the same time and later reduce the electrode combinations to identify a smaller subset of electrodes that maintains the similar efficacy with less power consumption.

Therefore, e.g., in a post-trial setting, after determining that the plurality of electrical stimulation therapy parameter sets results in treatment of a condition of patient 12, processing circuitry 210 of IMD 102 may select one or more electrical stimulation therapy parameter sets and/or electrodes to deactivate, such that the number of target tissue sites receiving electrical stimulation therapy is reduced. As an example of the above, and with respect to FIG. 1, processing circuitry 210 of IMD 102 provides electrical stimulation therapy to target tissue sites 14A-14D and 15A-15D. If the electrical stimulation therapy is determined to treat a condition of patient 12, processing circuitry 210 of IMD 102 deactivates electrodes providing electrical stimulation to target tissue sites 14A-14D such that only target tissue sites 15A-15D receive electrical stimulation.

If, subsequently, the electrical stimulation no longer treats the condition of patient 12, then the dorsal root area of patient 12 likely lies within target tissue sites 14A-14D. In this case, processing circuitry 210 of IMD 102 deactivates electrodes providing electrical stimulation to target tissue sites 15A-15D and reactivates electrodes providing electrical stimulation to target tissue sites 14A-14D. If the electrical stimulation continues to treat the condition of patient 12, then the dorsal root area of patient 12 likely lies within target tissue sites 15A-15D. Thus, by selectively activating and deactivating subsets of electrodes such that different target tissue sites 14A-14D and 15A-15D selectively receive electrical stimulation, processing circuitry 210 of IMD may determine a minimum number of electrodes that stimulate the dorsal root of patient 12 so as to effectively treat the condition of patient 12. By only using the minimum number of electrodes necessary, IMD 102 may conserve power so as to maximize the battery life of IMD 102 and therefore minimize the number of recharge operations required for IMD 102.

Accordingly, the techniques of the disclosure allow an IMD 102 to deliver electrical stimulation to a large portion of a body of patient 12 so as to allow a clinician to quickly determine whether the electrical stimulation is effective in treating the condition of patient 12. Furthermore, the techniques of the disclosure allow a clinician to remove ineffective electrical stimulation programs and/or electrodes so as to reduce the power consumption of the electrical stimulation programs delivered to patient 12.

The architecture of IMD 102 illustrated in FIG. 2 is shown as an example. The techniques as set forth in this disclosure may be implemented in the example IMD 102 of FIG. 2, as well as other types of systems not described specifically herein. Nothing in this disclosure should be construed so as to limit the techniques of this disclosure to the example architecture illustrated by FIG. 2.

Figure 3:
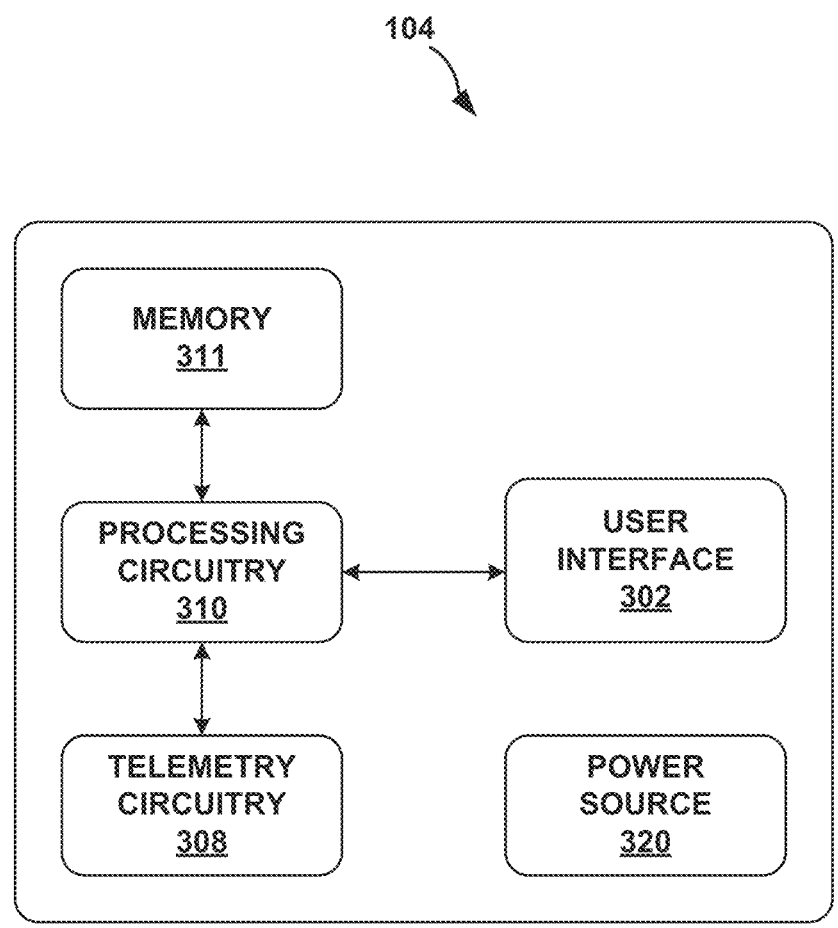
FIG. 3 is a block diagram of the example external programmer of FIG. 1.

FIG. 3 is a block diagram of the example external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or circuits, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, processing circuitry 310 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing processing circuitry 310 to perform the actions attributed to it. Moreover, although processing circuitry 310 and telemetry circuitry 308 are described as separate circuits, in some examples, processing circuitry 310 and telemetry circuitry 308 are functionally integrated. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Processing circuitry 310 may also control user interface 302 to display information related to an anatomical atlas (e.g., an atlas of a reference anatomy) and patient-specific anatomy. For example, user interface 302 may display a representation of one or more atlas-defined anatomical structures over a representation (e.g., an image) of the specific patient anatomy. User interface 302 may present annotation tools for adjusting the structures of the atlas to the patient anatomy and receive user annotations indicating where the corresponding structures of the patient anatomy are located and/or where the atlas should be moved with respect to the patient anatomy. Processing circuitry 310 may then adjust the position and/or size of the structures of the atlas to more closely match (e.g., a best fit) to the user annotation. After the atlas has been adjusted, the user may refer to the atlas for locations of certain structures of the patient instead of needing to continually find desired structures based on the image of the patient anatomy.

Telemetry circuitry 308 may support wireless communication between IMD 102 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 308 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

According to the techniques of the disclosure, user interface 302 of external programmer 104 receives a selection from a clinician of one or more combinations of electrodes for delivery of electrical stimulation therapy according to a plurality of electrical stimulation therapy parameter sets to patient 12. In response to the selection, processing circuitry 310, via telemetry circuitry 308, issues instructions to IMD 102 to deliver the electrical stimulation therapy according to the plurality of electrical stimulation therapy parameter sets. In response to the instructions, IMD 102 delivers to the target tissue areas electrical stimulation programs. In some examples, user interface 302 allows for a clinician to select one or more combinations of anode and cathode electrodes for the delivery of each electrical stimulation therapy program. In other examples, user interface 302 allows for a clinician to select a stimulation program including a desired target tissue area and desired effective frequency, and processing circuitry 310 automatically determines the appropriate combination of anode and cathode electrodes in multiple electrode combinations of IMD 102 to achieve the selected stimulation program. In this example, processing circuitry 310, via telemetry circuitry 308, issues instructions to IMD 102 causing IMD 102 to select the appropriate combination of anode and cathode electrodes and deliver electrical stimulation therapy according to a plurality of electrical stimulation therapy parameter sets.

The architecture of programmer 104 illustrated in FIG. 3 is shown as an example. The techniques as set forth in this disclosure may be implemented in the example programmer 104 of FIG. 3, as well as other types of systems not described specifically herein. Nothing in this disclosure should be construed so as to limit the techniques of this disclosure to the example architecture illustrated by FIG. 3.

Figure 4:
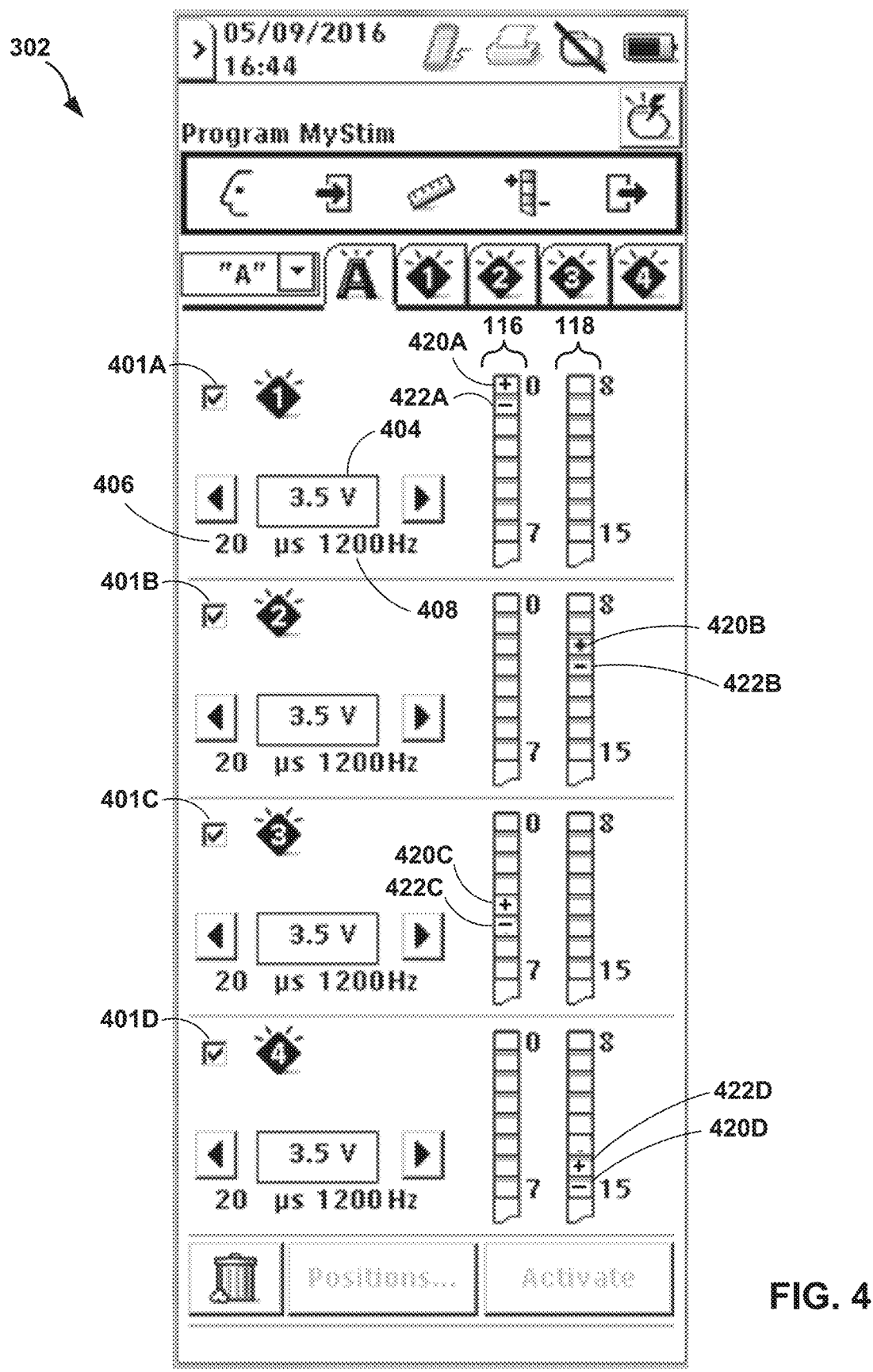
FIG. 4 is an illustration depicting an example user interface for an external programmer of FIG. 1.
Figure 6:
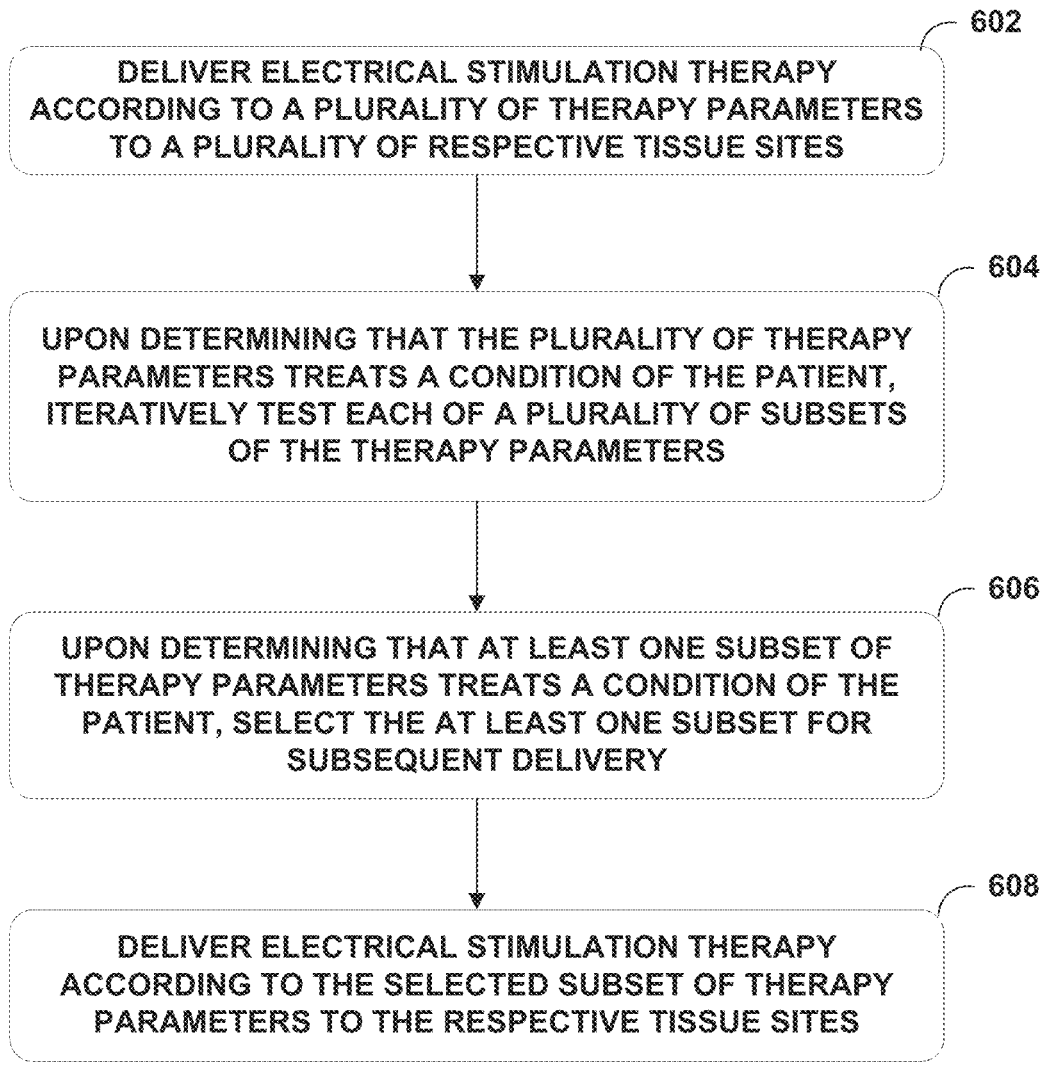
FIG. 6 is a flowchart illustrating an example operation according to the techniques of the disclosure.

FIG. 4 is an illustration depicting an example user interface 302 for an external programmer 104 of FIG. 1. In the example of FIG. 4, User interface 302 of FIG. 6 provides representations 401A-401D (collectively, "representations 401") of electrodes 116, 118 of IMD 102 of FIG. 2 carried on axial leads. Each representation of electrodes 116, 118 displays a plurality of electrodes 116 and the configuration of each of the plurality of electrodes 116 for a respective first, second, third, and fourth electrical stimulation therapy program whose stimulation pulses may be delivered simultaneously or on a time-interleaved basis. In response to commands from a clinician, external programmer 104 may configure one or more of electrodes 116 to function as anodic or cathodic electrodes for a particular electrical stimulation therapy program. In the example of FIG. 4, user interface 302 of external programmer 104 displays electrode 420A as an anodic electrode and electrode 422A as a cathodic electrode for the first stimulation program. Further, user interface 302 of external programmer 104 displays electrode 420B as an anodic electrode and electrode 422B as a cathodic electrode for the second stimulation program. Further, user interface 302 of external programmer 104 displays electrode 420C as an anodic electrode and electrode 422C as a cathodic electrode for the third stimulation program. Further, user interface 302 of external programmer 104 displays electrode 420D as an anodic electrode and electrode 422D as a cathodic electrode for the fourth stimulation program. As illustrated in FIG. 4, each of the anodic electrodes 420A-420D and cathodic electrodes 422A-422D are different electrodes and unique to the stimulation program.

User interface 302 provides selection buttons 401A-401D for receiving a command from a clinician to enable or disable a respective first, second, third, and fourth electrical stimulation therapy program for delivering electrical stimulation pulses to patient 12. User interface 302 further provides a selection box 404 for receiving a command from a clinician causing external programmer 104 to adjust the amplitude of the respective electrical stimulation therapy program. In the example of FIG. 4, selection box 404 controls a voltage amplitude. However, in other examples, selection box 404 controls a current amplitude. User interface 302 further provides a pulse width indicator 406 for displaying the pulse width of electrical pulses of the respective electrical stimulation therapy program and a frequency indicator 408 for displaying the frequency of electrical pulses of the respective electrical stimulation therapy program. In some examples, user interface 404 provides means to adjust the pulse width and frequency of electrical pulses of the respective electrical stimulation therapy program.

While the example of FIG. 4 provides for a sixteen-electrode system, the example of FIG. 4 has eight electrodes of the sixteen electrodes active and therefore provides for four simultaneous electrical stimulation programs. However, other systems may have any number of configurable electrodes and programs. As one example, another 16-electrode system allows from one to eight programs to run simultaneously on unique pairs of electrodes. Further, such a system may allow 16 programs to run simultaneously, wherein the case or housing of the IMD functions as an anode. As a further example, a 32-electrode system allows from one to 16 programs to run simultaneously on unique pairs of electrodes. Further, such a system may allow 32 programs to run simultaneously, wherein the case or housing of the IMD functions as the anode. Although each program in FIG. 4 is shown as including one cathode and one anode as a pair of electrodes, a single program may define an electrode combination with three or more electrodes that have the same or a different number of cathodes and anodes.

Accordingly, as described herein, a clinician may use an external programmer 104 to instruct an IMD 102 to deliver a plurality of electrical stimulation therapy programs to a plurality of tissue sites of patient 12. By delivering a plurality of such electrical stimulation therapy programs to a plurality of tissue sites, IMD 102 may effectively provide stimulation to large portions of spinal cord 20, therefore ensuring that at least some electrodes 116, 118 deliver electrical stimulation to a region of spinal cord 20 that effectively treats the condition of patient 12.

Figure 5A:
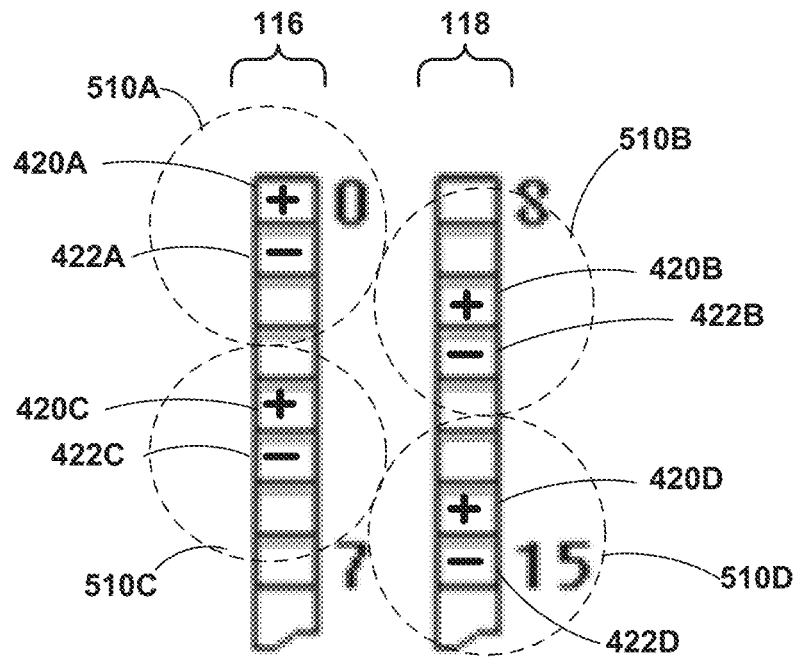
FIGS. 5A-5B are illustrations depicting example electrode leads of the IMD of FIG. 1.
Figure 5B:
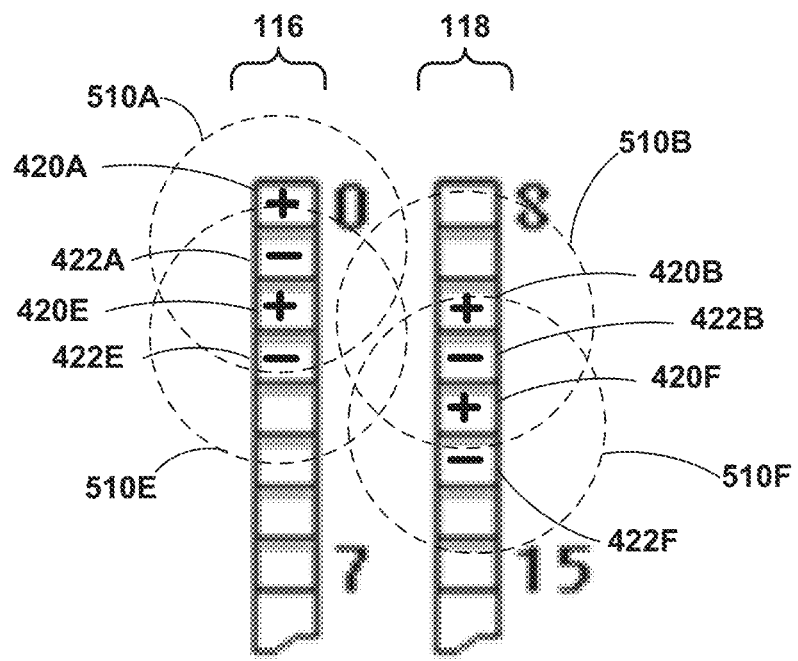

FIGS. 5A-5B are illustrations depicting example electrode leads of the IMD 102 of FIG. 1. In the example of FIG. 5A, electrodes 116, 118 are configured in a substantially similar fashion to the electrodes depicted by user interface 302 of FIG. 4. For example, electrode 420A is configured as an anodic electrode and electrode 422A as a cathodic electrode for the first stimulation program. Further, user interface 302 of external programmer 104 displays electrode 420B as an anodic electrode and electrode 422B is configured as a cathodic electrode for the second stimulation program. Further, electrode 420C is configured as an anodic electrode and electrode 422C is configured as a cathodic electrode for the third stimulation program. Further, electrode 420D is configured as an anodic electrode and electrode 422D is configured as a cathodic electrode for the fourth stimulation program. As illustrated in FIG. 4, each of the anodic electrodes 420A-420D and cathodic electrodes 422A-422D are different electrodes and unique to the stimulation program.

In the example configuration of FIG. 5A, external programmer 104 has configured each of the first, second, third, and fourth electrical stimulation therapy programs to deliver electrical pulses at 1000 Hertz. In other words, each pair of electrodes 420 and 422 deliver electrical pulses at 1000 Hertz. Therefore, tissue at the site of each pair of electrodes 420 and 422 receive electrical stimulation pulses at 1000 Hertz within a certain distance from the respective pair of electrodes. FIG. 5A further depicts zones of stimulation 510A-510D, which represent zones of tissue stimulation that may be affected by each of the respective pair of electrodes 420A-420D and 422A-422D. Zones of stimulation 510A-510D may represent an electrical field (e.g., voltage or current propagation) or an activation field showing nerves activated by the electrical field applied by the respective electrodes. Although zones of stimulation 510A-510D are shown as separate or not overlapping, two or more zones of stimulation 510A-510D may overlap in other examples based on the voltage or current amplitude, proximity of electrodes, tissue characteristics, or any other factors.

As described herein, a clinician may use an external programmer 104 to instruct IMD 102 to deliver electrical pulse trains comprising a plurality of electrical stimulation therapy programs to a plurality of tissue sites of patient 12. By delivering a plurality of such electrical pulse trains to a plurality of tissue sites, IMD 102 may effectively provide stimulation to large portions of spinal cord 20, therefore ensuring that at least some electrodes 116, 118 deliver electrical stimulation to a region of spinal cord 20 that effectively treat the condition of patient 12.

In the example of FIG. 5B, electrodes 116, 118 are configured in a substantially similar fashion to the electrodes depicted by user interface 302 of FIG. 4 and as depicted in FIG. 5A. However, in the example of FIG. 5B, IMD 102 has selected a different set of electrode pairs 116, 118 such that zones of stimulation 510A, 510B, 510E, and 510F cover less tissue area than the zones of stimulation 510A-510D of FIG. 5A. As described herein, IMD 102 may select different combinations of electrodes 116, 118 to test the different pairs of electrodes 116, 118 for their efficacy in effectively treating the condition of patient 12. For example, as described herein, IMD 102 may remove combinations of electrodes 116, 118 that do not treat the condition of patient 12 so as to minimize energy consumption by IMD 102. As a further example, IMD 102 may select different combinations of electrodes 116, 118 that generate zones of stimulation 510 to cover a small tissue area of patient 12 (e.g., the electrode combinations are closer together) so as to reduce one or more side effects that occur with pairs of electrodes that generate zones of stimulation 510 that cover a large tissue area of patient 12. Zones of stimulation 510A, 510B, 510E, and 510F may represent an electrical field (e.g., voltage or current propagation) or an activation field showing nerves activated by the electrical field applied by the respective electrodes. Although some zones of stimulation 510A, 510B, 510E, and 510F are shown as overlapping, one or more (e.g., all in some examples) zones of stimulation 510A, 510B, 510E, and 510F may not overlap each other (e.g., each zone covers distinct or separate areas of tissue) based on the voltage or current amplitude, proximity of electrodes, tissue characteristics, or any other factors. As discussed herein, for certainly pulse frequencies for example, it should be noted that tissue subject to two or more zones of stimulation (e.g., overlapping zones) may not respond differently than if the tissue was only subject to a single zone of stimulation. In such examples, the tissue (e.g., one or more nerves) receiving overlapping zones of stimulation may not be affected by removal of one or more overlapping zones as long as the tissue is still subject to a single remaining zone of stimulation.

FIG. 6 is a flowchart illustrating an example operation according to the techniques of the disclosure. For convenience, FIG. 6 is described with respect to IMD 102 of FIGS. 1 and 2. However, the techniques of FIG. 6 may be performed different components of IMD 102 or by additional or alternative medical devices.

In the example of FIG. 6, IMD 102 delivers electrical stimulation therapy according to a plurality of electrical stimulation therapy parameter sets to a plurality of tissue sites 14A-14D and 15A-15D of patient 12 (602). In one example, IMD 102 delivers electrical stimulation therapy according to each of the plurality of electrical stimulation therapy parameter sets via a respective combination of a plurality of electrodes 116, 118. In further examples, each combination of electrodes comprises a pair of electrodes. In some examples, each combination of electrodes comprises at least two electrodes, including one or more anodes and one or more cathodes.

The clinician determines whether the plurality of electrical stimulation therapy parameter sets was effective in treating the condition of patient 12. This may occur during a trial period in which the IMD 102 may be external from the patient or implanted. In some examples, the patient provides feedback to the clinician that the plurality of electrical stimulation therapy parameter sets caused a reduction in a pain sensation. In other examples, the clinician may determine whether the plurality of electrical stimulation therapy parameter sets was effective by observing a bioelectrical response of patient 12, such as a response of a nerve or muscle tissue to the plurality of electrical stimulation therapy parameter sets. In some examples, the clinician determines whether the plurality of electrical stimulation therapy parameter sets was effective during an implantation procedure where IMD 102 is implanted within patient 12.

In yet further examples, patient 12 provides feedback indicating that the plurality of electrical stimulation therapy parameter sets caused a reduction in a pain sensation. For example, after delivering electrical stimulation therapy according to the plurality of electrical stimulation therapy parameter sets, external programmer 104 provides, via user interface 302, a prompt for patient 12 to provide the feedback. In alternate examples, external programmer 104 may periodically (e.g., once per day, once per week) provide the prompt to patient 12. External programmer 104 receives, via user interface 302, the feedback indicating the effectiveness of the plurality of electrical stimulation therapy parameter sets. In some examples, the patient feedback may be a pain rating or estimation of pain relative to a pain scale. In some examples, external programmer 104 transmits the patient feedback to IMD 102.

In further examples, after delivering electrical stimulation therapy according to the plurality of electrical stimulation therapy parameter sets, IMD 102 uses one or more accelerometers to determine that the plurality of electrical stimulation therapy parameter sets was effective in treating the condition of patient 12. In still further examples, after delivering electrical stimulation therapy according to the plurality of electrical stimulation therapy parameter sets, IMD 102 may use data from the one or more accelerometers to evaluate functionality of the patient, such as tremor, gait, flexibility, wrist flexion, or patient movement, to determine whether the severity of the condition of patient 12 has improved or gotten worse.

Upon determining that the plurality of electrical stimulation therapy parameter sets was effective in treating the condition of patient 12, IMD 102 iteratively tests each of a plurality of subsets of the electrical stimulation therapy parameter sets via a subset of combinations of electrodes 116, 118 to a subset of tissue sites 14A-14D and 15A-15D of patient 12 (604). In some examples, IMD 102 performs such iterative testing during a chronic period of time in which the patient is receiving therapy due to electrical stimulation therapy according to the plurality of electrical stimulation therapy parameter sets being effective at treating the patient condition. For example, this chronic period may be post-trial and after implantation of IMD 102 within patient 12.

In some examples, as described above, for each of the plurality of subsets of the electrical stimulation therapy parameter sets, external programmer 104 prompts patient 12 for feedback which of the plurality of electrical stimulation therapy parameter sets are effective in treating the condition of patient 12. In this example, external programmer 104 receives such patient feedback and transmits the patient feedback to IMD 102. IMD 102, based on the patient feedback, selects further subsets of the electrical stimulation therapy parameter sets for delivery of the electrical stimulation. In alternate examples, IMD 102 compares the accelerometer data for each of the plurality of electrical stimulation therapy parameter sets in the manner described above to determine which of the plurality of electrical stimulation therapy parameter sets are effective in treating the condition of patient 12. For example, by detecting an increased amount of activity by patient 12, IMD 102 may determine that patient 12 is suffering less pain (e.g., thereby allowing for patient 12 to engage in more activity). As a contrasting example, by detecting a decreased amount of activity by patient 12, IMD 102 may determine that patient 12 is suffering more pain (e.g., thereby preventing activity by patient 12). In this example, IMD 102, based on such accelerometer data, selects further subsets of the electrical stimulation therapy parameter sets for delivery of the electrical stimulation.

As one example, IMD 102 may deactivate at least one first combination of plurality of electrodes 116, 118 (or deactivate a therapy program defining the first combination of electrodes) such that at least one first electrical stimulation therapy parameter set of the plurality of electrical stimulation therapy parameter sets is not delivered to patient 12. IMD 102 may deliver electrical stimulation therapy according to the remaining electrical stimulation therapy parameter sets via the remaining combinations of electrodes 116, 118 and determine an effectiveness of the remaining electrical stimulation therapy parameter sets at treating the condition of patient 12. Further, IMD 102 may reactivate the at least one first electrode combination of plurality of electrodes 116, 118 and deactivate at least one second electrode combination of plurality of electrodes 116, 118. IMD 102 may deliver electrical stimulation therapy according to the remaining electrical stimulation therapy parameter sets via the remaining combinations of electrodes 116, 118 and determine an effectiveness of the remaining electrical stimulation therapy parameter sets at treating the condition of patient 12. In this fashion, IMD 102 may test the effectiveness of each combination of electrodes 116, 118 in treating the condition of patient 12.

In another example, IMD 102 may deactivate one half of the combinations of electrodes 116, 118 such that electrical stimulation therapy defined by a first half of the plurality of electrical stimulation therapy parameter sets is not delivered to patient 12. IMD 102 may deliver electrical stimulation therapy according to the remaining electrical stimulation therapy parameter sets via the remaining combinations of electrodes 116, 118 and determine an effectiveness of the remaining electrical stimulation therapy parameter sets at treating the condition of patient 12. If the remaining electrical stimulation therapy parameter sets are effective at treating the condition of patient 12, the first half of the plurality of electrical stimulation therapy parameter sets may not be necessary to provide therapy to patient 12, and may be deactivated to conserve power. If the remaining electrical stimulation therapy parameter sets are not effective at treating the condition of patient 12, then the first half of the plurality of electrical stimulation therapy parameter sets may be necessary to provide therapy to patient 12 and may be reactivated. Further, the remaining electrical stimulation therapy parameter sets may not be necessary to provide therapy to patient 12 and may be deactivated to conserve power.

Upon determining that at least one subset of electrical stimulation therapy parameter sets treats the condition of patient 12, IMD 102 selects at least one subset of electrical stimulation therapy parameter sets for defining subsequent delivery of electrical stimulation to patient 12 (606) for chronic stimulation therapy. IMD 102 deactivates the combinations of electrodes 116, 118 that deliver electrical stimulation therapy determined not to be necessary for providing therapy to patient 112. Further, IMD 102 delivers electrical stimulation therapy according to the at least one subset of electrical stimulation therapy parameter sets to patient 12 via the respective combinations of electrodes 116, 118. In some examples, IMD 102 may perform such an iterative testing of the plurality of electrical stimulation therapy parameter sets on a periodic basis, such as daily, weekly, or monthly, so as to periodically determine a subset of electrical stimulation therapy parameter sets that provides effective therapy to patient 12 but uses a minimal number of electrode combinations, and therefore a minimal amount of power.

Figure 7:
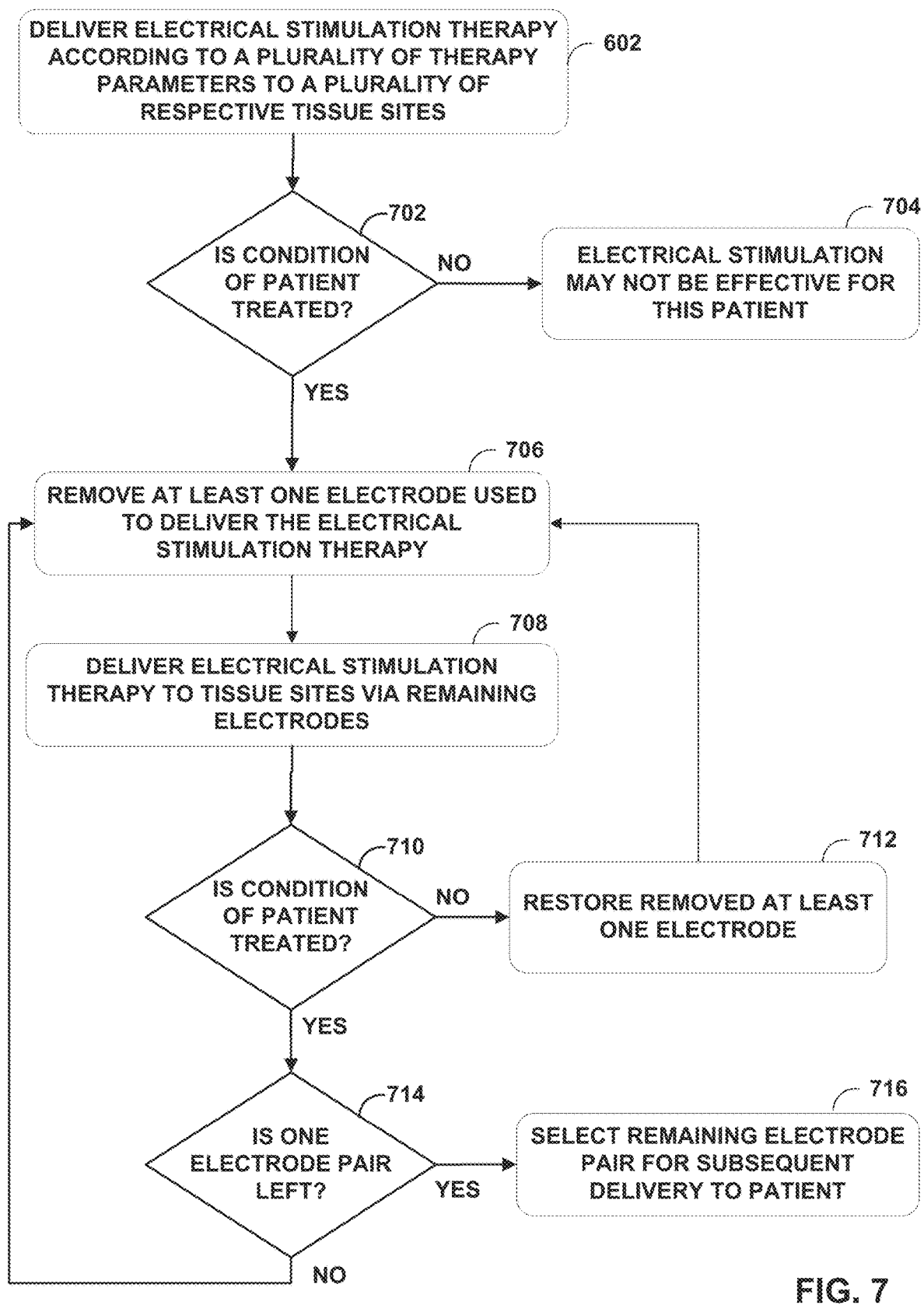
FIG. 7 is a flowchart illustrating an example operation according to the techniques of the disclosure.

FIG. 7 is a flowchart illustrating an example operation according to the techniques of the disclosure. For convenience, FIG. 7 is described with respect to IMD 102 of FIGS. 1 and 2. However, the techniques of FIG. 7 may be performed different components of IMD 102 or by additional or alternative medical devices.

In the example of FIG. 7, IMD 102 delivers electrical stimulation according to a plurality of electrical stimulation therapy parameter sets to a plurality of tissue sites 14A-14D and 15A-15D of patient 12, as described above with respect to 602 of FIG. 6. A clinician determines whether the plurality of electrical stimulation therapy parameter sets was effective in treating the condition of patient 12 (702). In some examples, the patient provides feedback to the clinician that the plurality of electrical stimulation therapy parameter sets caused a reduction in a pain sensation. In other examples, the clinician may determine whether the plurality of electrical stimulation therapy parameter sets was effective by observing a bioelectrical response of patient 12, such as a response of a nerve or muscle tissue to the plurality of electrical stimulation therapy parameter sets. In some examples, the clinician determines whether the plurality of electrical stimulation therapy parameter sets is effective during an implantation procedure where IMD 102 is implanted within patient 12. In yet further examples, external programmer 104 receives, from patient 12, feedback indicating that the plurality of electrical stimulation therapy parameter sets was effective. External programmer 104 transmits such feedback to IMD 102.

If the plurality of electrical stimulation therapy parameter sets does not treat the condition of patient 12 (e.g., "NO" block of 702), then electrical stimulation may not be effective in providing therapy to patient 12 (704). The clinician may attempt to try an alternative therapy, such as different frequencies, amplitudes, or pulse widths, or try implanting electrodes at different tissue sites. Otherwise, the clinician may determine that the patient does not respond to high frequency electrical stimulation. However, if the plurality of electrical stimulation therapy parameter sets does treat the condition of patient 12 (e.g., "YES" block of 702), then electrical stimulation is effective in providing therapy to patient 12, and IMD 102 may iteratively test different electrical stimulation therapy parameter sets so as to minimize the power usage of the system.

As one example, IMD 102 removes at least one of electrodes 116, 118 used to deliver the electrical stimulation therapy according to the plurality of electrical stimulation therapy parameter sets (706). In one example, IMD 102 removes a single one of electrodes 116, 118 (e.g., in a multipolar electrode configuration) or a single pair of electrodes 116, 118 (e.g., in a bipolar electrode configuration) such that patient 12 does not receive electrical stimulation therapy according to a single electrical stimulation therapy parameter set of the plurality of electrical stimulation therapy parameter sets. In an example bipolar configuration, a pair of electrodes includes two electrodes 116, 118. In an example unipolar configuration, a pair of electrodes includes one electrode 116, 118 and a housing of IMD 102. Instead of removing electrodes, IMD 102 may achieve the same result by removing one or more therapy programs that define one or more electrode combinations. In another example, IMD 102 removes half of electrodes 116, 118 such that patient 12 does not receive electrical stimulation therapy defined by half of the plurality of electrical stimulation therapy parameter sets. IMD 102 delivers the electrical stimulation therapy according to the remaining electrical stimulation therapy parameter sets to tissue sites 14A-14D and 15A-15D of patient 12 via the remaining electrodes 116, 118 (708).

IMD 112 determines whether the remaining electrical stimulation therapy parameter sets treat the condition of patient 12 (710). If the remaining electrical stimulation therapy parameter sets do not treat the condition of patient 12 (e.g., "NO" block of 710), then IMD 102 restores the removed at least one of electrodes 116, 118 (712) and removes at least one different electrode of electrodes 116, 118 (712). It should be noted that if removal of a single therapy program or single electrode combination eliminates effective therapy for patient 12, IMD 102 may identify this change as that single therapy program or single electrode combination as being responsible for effective therapy and proceed to block 708 by delivering stimulation with only those electrodes that were previously removed and are likely responsible for effective therapy. IMD 102 delivers electrical stimulation therapy according to the remaining electrical stimulation therapy parameter sets (708) and determines whether the remaining electrical stimulation therapy parameter sets treat the condition of patient 12 (710).

If the remaining electrical stimulation therapy parameter sets treat the condition of patient 12 (e.g., "YES" block of 710), then IMD 102 determines whether the remaining electrical stimulation therapy parameter sets are delivered via a single pair of electrodes 116, 118 (714) (e.g., for a bipolar configuration, two electrodes 116, 118, and for a unipolar combination, one of electrodes 116, 118 and a housing of IMD 102). If IMD 102 is delivering electrical stimulation therapy according to the electrical stimulation therapy parameter sets via two or more pairs of electrodes 116, 118 (e.g., "NO" block of 714), then IMD 102 attempts to remove one of the pairs as discussed above. If IMD 102 is delivering electrical stimulation therapy according to the electrical stimulation therapy parameter sets via a single pair of electrodes 116, 118 (e.g., "YES" block of 714), then IMD 102 selects the remaining pair of electrodes 116, 118 for subsequent delivery of electrical stimulation therapy according to a respective electrical stimulation therapy parameter set to patient 12. Although "pairs" of electrodes are described with respect to the process of FIG. 7, IMD 102 may remove individual electrodes or remove therapy programs that define combinations of two or more electrodes.

Figure 8:
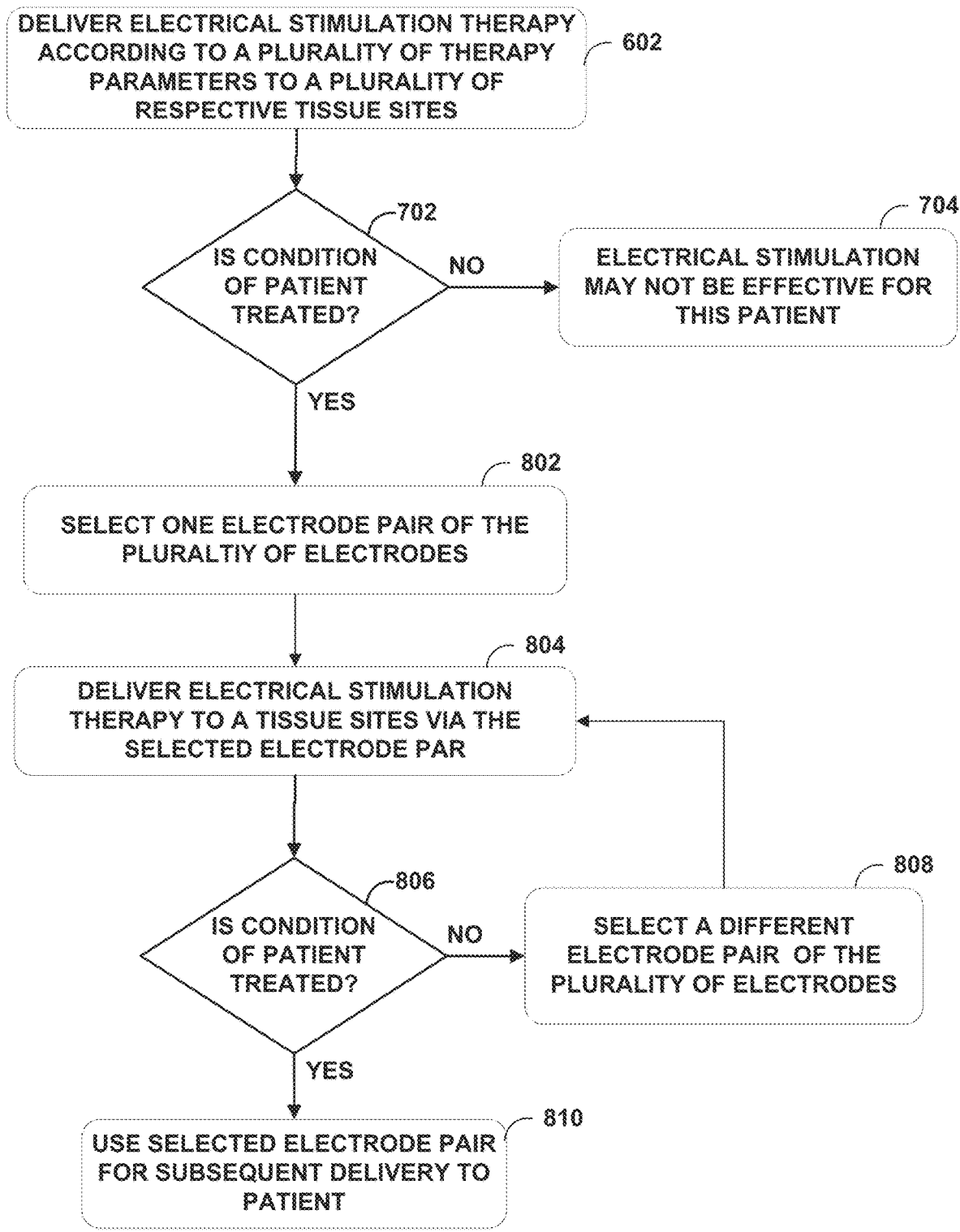
FIG. 8 is a flowchart illustrating an example operation according to the techniques of the disclosure.

FIG. 8 is a flowchart illustrating an example operation according to the techniques of the disclosure. For convenience, FIG. 8 is described with respect to IMD 102 of FIGS. 1 and 2. However, the techniques of FIG. 8 may be performed different components of IMD 102 or by additional or alternative medical devices.

In the example of FIG. 8, IMD 102 delivers electrical stimulation therapy according to a plurality of electrical stimulation therapy parameter sets to a plurality of tissue sites 14A-14D and 15A-15D of patient 12, as described above with respect to FIG. 6 (602). A clinician determines whether or not the plurality of electrical stimulation therapy parameter sets was effective in treating the condition of patient 12, as described with respect to blocks 702 and 704 of FIG. 7.

If the plurality of electrical stimulation therapy parameter sets treat the condition of patient 12 (e.g., "YES" block of 702), then electrical stimulation is effective in providing therapy to patient 12, and IMD 102 may iteratively test different electrical stimulation therapy parameter sets so as to minimize the power usage of the system. For example, IMD 102 selects one pair of electrodes 116, 118 of the plurality of electrodes 116, 118 (802). IMD 102 delivers electrical stimulation therapy via the selected pair of electrodes 116, 118 to a respective target tissue site of tissue sites 14A-14D and 15A-15D of patient 12 (804). IMD 112 determines whether the delivered electrical stimulation therapy treats the condition of patient 12 (806).

If the delivered electrical stimulation therapy does not treat the condition of patient 12 (e.g., "NO" block of 710), then IMD 102 selects a different pair of electrodes 116, 118 of the plurality of electrodes 116, 118 (808). IMD 102 delivers electrical stimulation therapy via the different pair of electrodes 116, 118 to a respective target tissue site of tissue sites 14A-14D and 15A-15D of patient 12 (804). If the delivered electrical stimulation therapy treats the condition of patient 12 (e.g., "YES" block of 710), then IMD 102 uses the selected pair of electrodes 116, 118 of the plurality of electrodes 116, 118 for subsequent delivery of electrical stimulation to patient 12 (810). In some examples, if single electrode pairs do not maintain the effective therapy provided by the original plurality of electrical stimulation therapy parameter sets, then IMD 102 may iteratively try two or more electrode pairs until a combination of electrodes is identified that elicits the previously identified effective therapy.

While in this example, IMD 102 iteratively tests a single pair of electrodes 116, 118 of the plurality of combination of electrodes 116, 118, in other examples, IMD 102 may iteratively test two or more pairs of electrodes 116, 118 or a group of three or more electrodes (e.g., a group of three or more electrodes comprising at least one or more anode electrodes and one or more cathode electrodes). Upon determining a subset of two or more pairs of electrodes 116, 118 that effectively treats the condition of patient 12, IMD 102 may further test individual pairs of electrodes 116, 118 within the subset of two or more pairs of electrodes 116, 118 so as to further reduce the number of electrodes 116, 118 that are used to effectively deliver electrical stimulation to patient 12.

The following examples illustrate one or more aspects of the disclosure.

Example 1. A method comprising: delivering, by a medical device via a plurality of electrodes, a plurality of electrical stimulation therapies to a plurality of respective tissue sites of a patient, the plurality of electrical stimulation therapies treating a condition of the patient; subsequent to delivering the plurality of electrical stimulation therapies, selecting a plurality of subsets of the plurality of electrical stimulation therapies, wherein each subset of the plurality of electrical stimulation therapies includes at least one electrical stimulation therapy of the plurality of electrical stimulation therapies and less than all of the plurality of electrical stimulation therapies, and wherein each subset of the plurality of electrical stimulation therapies is delivered via a respective set of electrodes different from sets of electrodes that deliver other subsets of the plurality of electrical stimulation therapies; iteratively delivering, by the medical device, the subsets of the plurality of electrical stimulation therapies to the patient via the respective sets of electrodes; and selecting at least one subset of the plurality of electrical stimulation therapies that treat the condition of the patient for subsequent delivery to the patient.

Example 2. The method of example 1, further comprising delivering the selected at least one subset of the plurality of electrical stimulation therapies to the patient for a chronic period of time to treat the condition of the patient, wherein the plurality of electrical stimulation therapies is delivered for a trial period of time shorter than the chronic period of time.

Example 3. The method of any of examples 1-2, wherein iteratively delivering the subsets of the plurality of electrical stimulation therapies via the respective sets of electrodes comprises iteratively delivering the subsets of the plurality of electrical stimulation therapies via the respective sets of electrodes to a respective subset of the plurality of respective tissue sites, wherein each subset of the plurality of respective tissue sites does not include at least one tissue site of the plurality of respective tissue sites and is different from each other subset of the plurality of respective tissue sites.

Example 4. The method of any of examples 1-3, wherein each respective set of electrodes via which the subsets of the plurality of electrical stimulation therapies are delivered consists of a single cathode and a single cathode.

Example 5. The method of any of examples 1-4, wherein treating the condition of the patient comprises reducing pain of the patient without substantially producing paresthesia in the patient.

Example 6. The method of any of examples 1-5, wherein the plurality of tissue sites of the patient comprise at least a T9 vertebrae region of a spinal cord of the patient and a T10 vertebrae region of the spinal cord of the patient.

Example 7. The method of any of examples 1-6, wherein each electrical stimulation therapy of the plurality of electrical stimulation therapies comprises at least first electrical stimulation pulses at a first frequency greater than about 600 Hertz and less than about 1,500 Hertz interleaved with second electrical stimulation pulses at a second frequency greater than about 600 Hertz and less than about 1,500 Hertz to form a combined pulse train with a combined pulse frequency of greater than approximately 1,500 Hertz.

Example 8. The method of any of examples 1-6, wherein each electrical stimulation therapy of the plurality of electrical stimulation therapies comprises electrical stimulation pulses comprising a pulse frequency greater than about 600 Hz.

Example 9. The method of any of examples 1-6, wherein each electrical stimulation therapy of the plurality of electrical stimulation therapies comprises electrical stimulation pulses comprising a pulse frequency greater than about 1000 Hz.

Example 10. The method of any of examples 1-9, wherein selecting the plurality of subsets of the plurality of electrical stimulation therapies and iteratively delivering the subsets of the plurality of electrical stimulation therapies comprises iteratively: removing at least one subset of the plurality of subsets of the plurality of electrical stimulation therapies; and delivering the remaining subsets of the plurality of electrical stimulation therapies to the patient via the respective sets of electrodes.

Example 11. The method of any of examples 1-9, wherein selecting the plurality of subsets of the plurality of electrical stimulation therapies and iteratively delivering the subsets of the plurality of electrical stimulation therapies comprises iteratively: selecting at least one subset of the plurality of subsets of the plurality of electrical stimulation therapies; and delivering the selected at least one subset of the plurality of subsets of the plurality of electrical stimulation therapies to the patient via the respective sets of electrodes.

Example 12. The method of any of examples 1-11, wherein delivering the plurality of electrical stimulation therapies comprises delivering, by the medical device, all electrical stimulation therapies of the plurality of electrical stimulation therapies substantially simultaneously with each other.

Example 13. The method of any of examples 1-11, wherein delivering the plurality of electrical stimulation therapies comprises delivering, by the medical device, each electrical stimulation therapy of the plurality of electrical stimulation therapies on a time-interleaved basis with other electrical stimulation therapies of the plurality of electrical stimulation therapies.

Example 14. The method of any of examples 1-13, wherein selecting the at least one subset of the plurality of electrical stimulation therapies that treat the condition of the patient for subsequent delivery to the patient comprises selecting, based on feedback from the patient, the at least one subset of the plurality of electrical stimulation therapies that treat the condition of the patient for subsequent delivery to the patient.

Example 15. The method of any of examples 1-14, further comprising, generating, via one or more accelerometers of the medical device and for each of the subsets of the plurality of electrical stimulation therapies, accelerometer data indicating activity of the patient during delivery of the respective electrical stimulation therapies, wherein selecting the at least one subset of the plurality of electrical stimulation therapies that treat the condition of the patient for subsequent delivery to the patient comprises selecting, based on the accelerometer data, the at least one subset of the plurality of electrical stimulation therapies that treat the condition of the patient for subsequent delivery to the patient.

Example 16. A medical device system comprising: stimulation circuitry of a medical device configured to deliver, via a plurality of electrodes, a plurality of electrical stimulation therapies to a plurality of respective tissue sites of a patient, the plurality of electrical stimulation therapies treating a condition of the patient; and processing circuitry configured to: subsequent to delivering the plurality of electrical stimulation therapies, select a plurality of subsets of the plurality of electrical stimulation therapies, wherein each subset of the plurality of electrical stimulation therapies includes at least one electrical stimulation therapy of the plurality of electrical stimulation therapies and less than all of the plurality of electrical stimulation therapies, and wherein each subset of the plurality of electrical stimulation therapies is delivered via a respective set of electrodes different from sets of electrodes that deliver other subsets of the plurality of electrical stimulation therapies; iteratively control delivery, by the stimulation circuitry of the medical device, the subsets of the plurality of electrical stimulation therapies to the patient via the respective sets of electrodes; and select at least one subset of the plurality of electrical stimulation therapies that treat the condition of the patient for subsequent delivery to the patient.

Example 17. The medical device system of example 16, wherein the processing circuitry is further configured to control delivery of the selected at least one subset of the plurality of electrical stimulation therapies to the patient for a chronic period of time to treat the condition of the patient, wherein the processing circuitry controls delivery of the plurality of electrical stimulation therapies for a trial period of time shorter than the chronic period of time.

Example 18. The medical device system of any of examples 16-17, wherein, to iteratively control delivery of the subsets of the plurality of electrical stimulation therapies via the respective sets of electrodes, the processing circuitry is further configured to iteratively control delivery of the subsets of the plurality of electrical stimulation therapies via the respective sets of electrodes to a respective subset of the plurality of respective tissue sites, wherein each subset of the plurality of respective tissue sites does not include at least one tissue site of the plurality of respective tissue sites and is different from each other subset of the plurality of respective tissue sites.

Example 19. The medical device system of any of examples 16-18, wherein each respective set of electrodes via which the subsets of the plurality of electrical stimulation therapies are delivered consists of a single cathode and a single cathode.

Example 20. The medical device system of any of examples 16-19, wherein, to treat the condition of the patient, the selected at least one subset of the plurality of electrical stimulation therapies reduces pain of the patient without substantially producing paresthesia in the patient.

Example 21. The medical device system of any of examples 16-20, wherein the plurality of tissue sites of the patient comprise at least a T9 vertebrae region of a spinal cord of the patient and a T10 vertebrae region of the spinal cord of the patient.

Example 22. The medical device system of any of examples 16-21, wherein each electrical stimulation therapy of the plurality of electrical stimulation therapies comprises at least first electrical stimulation pulses at a first frequency greater than about 600 Hertz and less than about 1,500 Hertz interleaved with second electrical stimulation pulses at a second frequency greater than about 600 Hertz and less than about 1,500 Hertz to form a combined pulse train with a combined pulse frequency of greater than approximately 1,500 Hertz.

Example 23. The medical device system of any of examples 16-21, wherein each electrical stimulation therapy of the plurality of electrical stimulation therapies comprises electrical stimulation pulses comprising a pulse frequency greater than about 600 Hz.

Example 24. The medical device system of any of examples 16-21, wherein each electrical stimulation therapy of the plurality of electrical stimulation therapies comprises electrical stimulation pulses comprising a pulse frequency greater than about 1000 Hz.

Example 25. The medical device system of any of examples 16-24, wherein, to select the plurality of subsets of the plurality of electrical stimulation therapies and iteratively control delivery of the subsets of the plurality of electrical stimulation therapies, the processing circuitry is further configured to iteratively: remove at least one subset of the plurality of subsets of the plurality of electrical stimulation therapies; and control delivery of the remaining subsets of the plurality of electrical stimulation therapies to the patient via the respective sets of electrodes.

Example 26. The medical device system of any of examples 16-24, wherein, to select the plurality of subsets of the plurality of electrical stimulation therapies and iteratively control delivery of the subsets of the plurality of electrical stimulation therapies, the processing circuitry is further configured to iteratively: select at least one subset of the plurality of subsets of the plurality of electrical stimulation therapies; and control delivery of the selected at least one subset of the plurality of subsets of the plurality of electrical stimulation therapies to the patient via the respective sets of electrodes.

Example 27. The medical device system of any of examples 16-26, wherein, to control delivery of the plurality of electrical stimulation therapies, the processing circuitry is further configured to control delivery of all electrical stimulation therapies of the plurality of electrical stimulation therapies substantially simultaneously with each other.

Example 28. The medical device system of any of examples 16-26, wherein, to control delivery of the plurality of electrical stimulation therapies, the processing circuitry is further configured to control delivery of each electrical stimulation therapy of the plurality of electrical stimulation therapies on a time-interleaved basis with other electrical stimulation therapies of the plurality of electrical stimulation therapies.

Example 29. The medical device system of any of examples 16-28, wherein, to select the at least one subset of the plurality of electrical stimulation therapies that treat the condition of the patient for subsequent delivery to the patient, the processing circuitry is further configured to select, based on feedback from the patient, the at least one subset of the plurality of electrical stimulation therapies that treat the condition of the patient for subsequent delivery to the patient.

Example 30. The medical device system of any of examples 16-29, wherein the medical device further comprises one or more accelerometers configured to generate, for each of the subsets of the plurality of electrical stimulation therapies, accelerometer data indicating activity of the patient during delivery of the respective electrical stimulation therapies; and wherein, to select the at least one subset of the plurality of electrical stimulation therapies that treat the condition of the patient for subsequent delivery to the patient, the processing circuitry is further configured to select, based on the accelerometer data, the at least one subset of the plurality of electrical stimulation therapies that treat the condition of the patient for subsequent delivery to the patient.

Example 31. A medical device system comprising: means for delivering, via a plurality of electrodes, a plurality of electrical stimulation therapies to a plurality of respective tissue sites of a patient, the plurality of electrical stimulation therapies treating a condition of the patient; means for, subsequent to delivering the plurality of electrical stimulation therapies, selecting a plurality of subsets of the plurality of electrical stimulation therapies, wherein each subset of the plurality of electrical stimulation therapies includes at least one electrical stimulation therapy of the plurality of electrical stimulation therapies and less than all of the plurality of electrical stimulation therapies, and wherein each subset of the plurality of electrical stimulation therapies is delivered via a respective set of electrodes different from sets of electrodes that deliver other subsets of the plurality of electrical stimulation therapies; means for iteratively delivering, by the medical device, the subsets of the plurality of electrical stimulation therapies to the patient via the respective sets of electrodes; and means for selecting at least one subset of the plurality of electrical stimulation therapies that treat the condition of the patient for subsequent delivery to the patient.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules, circuits, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical device system comprising:
stimulation circuitry of a medical device configured to deliver, via a plurality of electrodes, electrical stimulation therapy according to a plurality of therapy parameter sets to a plurality of respective tissue sites of a patient, the electrical stimulation therapy configured to treat a condition of the patient, and wherein the stimulation circuitry is configured to deliver the electrical stimulation therapy according to the plurality of therapy parameter sets by one of: simultaneously delivering the electrical stimulation therapy according to each therapy parameter set of the plurality of therapy parameter sets, or delivering the electrical stimulation therapy according to each therapy parameter set of the plurality of therapy parameter sets on a time-interleaved basis with other therapy parameter sets of the plurality of therapy parameter sets; and
processing circuitry configured to:
subsequent to delivering electrical stimulation therapy according to the plurality of therapy parameter sets, select a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets;
iteratively control delivery, by the stimulation circuitry of the medical device, of electrical stimulation therapy according to the subsets of the plurality of therapy parameter sets to the patient via the respective sets of electrodes;
determine, based on the iterative delivery of electrical stimulation therapy according to the subsets of the plurality of therapy sets, one or more subsets of the plurality of therapy parameters that treat the condition of the patient, wherein the one or more subsets are less than all of the subsets of the plurality of therapy parameter sets;
select the one or more subsets of the plurality of therapy parameter sets for defining subsequent electrical stimulation therapy to the patient; and
control the stimulation circuitry to deliver the subsequent electrical stimulation therapy to the patient according to the selected one or more subsets of the plurality of therapy parameter sets.

2. The medical device system of claim 1, wherein the processing circuitry is configured to receive, for each of the subsets of the plurality of therapy parameter sets, a respective patient parameter value from a sensor, and wherein the processing circuitry is configured to select the at least one subset of the plurality of therapy parameter sets by at least selecting, based on the respective patient parameter value, the at least one subset of the plurality of therapy parameter sets.

3. The medical device system of claim 2, wherein the sensor comprises at least one of an accelerometer, an optical sensor, a chemical sensor, or a temperature sensor.

4. The medical device system of claim 1, further comprising sensing circuitry configured to sense one or more bioelectric neural signals from the patient, and wherein the processing circuitry is configured to select the at least one subset of the plurality of therapy parameter sets by at least selecting, based on the one or more sensed bioelectric neural signals, the at least one subset of the plurality of therapy parameter sets.

5. The medical device system of claim 4, wherein the sensing circuitry is configured to sense the one or more bioelectric neural signals from the patient by at least sensing the one or more bioelectric neural signals from a spinal cord of the patient.

6. The medical device system of claim 1,
wherein the processing circuitry is configured to iteratively control delivery of the electrical stimulation therapy according to the subsets of the plurality of therapy parameter sets via the respective sets of electrodes by at least:

controlling delivery of electrical stimulation therapy according to a first subset of the plurality of therapy parameter sets;
determining that the first subset of the plurality of therapy parameter sets does not treat the condition of the patient;
controlling delivery of electrical stimulation therapy according to a second subset of the plurality of therapy parameter sets; and
determining that the second subset of the of the plurality of therapy parameter sets treats the condition of the patient; and
wherein the processing circuitry is configured to select the at least one subset of the plurality of therapy parameter sets that treat the condition of the patient for defining subsequent delivery of electrical stimulation therapy to the patient by at least selecting the second subset of the plurality of therapy parameter sets for defining subsequent delivery of electrical stimulation therapy to the patient.

7. The medical device system of claim 1, wherein the stimulation circuitry is configured to deliver electrical stimulation therapy according to the selected at least one subset of the plurality of therapy parameter sets to the patient for a chronic period of time to treat the condition of the patient, wherein the electrical stimulation therapy is delivered according to the plurality of therapy parameter sets for a trial period of time shorter than the chronic period of time.

8. The medical device system of claim 1, wherein the plurality of tissue sites of the patient comprise at least a T9 vertebrae region of a spinal cord of the patient and a T10 vertebrae region of the spinal cord of the patient.

9. The medical device system of claim 1, wherein each therapy parameter set of the plurality of therapy parameter sets defines electrical stimulation therapy comprising at least first electrical stimulation pulses at a first frequency greater than about 600 Hertz and less than about 1,500 Hertz interleaved with second electrical stimulation pulses at a second frequency greater than about 600 Hertz and less than about 1,500 Hertz to form a pulse train with a pulse frequency of greater than approximately 1,500 Hertz.

10. The medical device system of claim 1, wherein each therapy parameter set of the plurality of therapy parameter sets defines electrical stimulation therapy comprising electrical stimulation pulses comprising a pulse frequency greater than about 1000 Hz.

11. A method comprising:
delivering, by a medical device via a plurality of electrodes, electrical stimulation therapy according to a plurality of therapy parameter sets to a plurality of respective tissue sites of a patient, the electrical stimulation therapy configured to treat a condition of the patient, and wherein delivering the electrical stimulation therapy according to the plurality of therapy parameter sets comprises one of: simultaneously delivering the electrical stimulation therapy according to each therapy parameter set of the plurality of therapy parameter sets, or delivering the electrical stimulation therapy according to each therapy parameter set of the plurality of therapy parameter sets on a time-interleaved basis with other therapy parameter sets of the plurality of therapy parameter sets;
subsequent to delivering the electrical stimulation therapy according to the plurality of therapy parameter sets, selecting a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets;
determining, based on the iterative delivery of electrical stimulation therapy according to the subsets of the plurality of therapy sets, one or more subsets of the plurality of therapy parameters that treat the condition of the patient, wherein the one or more subsets are less than all of the subsets of the plurality of therapy parameter sets;
selecting the one or more subsets of the plurality of therapy parameter sets for defining subsequent electrical stimulation therapy to the patient; and
delivering, by the medical device, the subsequent electrical stimulation therapy to the patient according to the selected one or more subsets of the plurality of therapy parameter sets.

12. The method of claim 11, further comprising receiving, for each of the subsets of the plurality of therapy parameter sets, a respective patient parameter value from a sensor, and wherein selecting the at least one subset of the plurality of therapy parameter sets comprises selecting, based on the respective patient parameter value, the at least one subset of the plurality of therapy parameter sets.

13. The method of claim 12, wherein the sensor comprises at least one of an accelerometer, an optical sensor, a chemical sensor, or a temperature sensor.

14. The method of claim 11, further comprising sensing one or more bioelectric neural signals from the patient, and wherein selecting the at least one subset of the plurality of therapy parameter sets comprises selecting, based on the one or more sensed bioelectric neural signals, the at least one subset of the plurality of therapy parameter sets.

15. The method of claim 14, wherein sensing the one or more bioelectric neural signals from the patient comprises sensing the one or more bioelectric neural signals from a spinal cord of the patient.

16. The method of claim 11,
wherein iteratively delivering the electrical stimulation therapy according to the subsets of the plurality of therapy parameter sets via the respective sets of electrodes comprises:
delivering electrical stimulation therapy according to a first subset of the plurality of therapy parameter sets;
determining that the first subset of the plurality of therapy parameter sets does not treat the condition of the patient;
delivering electrical stimulation therapy according to a second subset of the plurality of therapy parameter sets; and
determining that the second subset of the of the plurality of therapy parameter sets treats the condition of the patient; and
wherein selecting the at least one subset of the plurality of therapy parameter sets that treat the condition of the patient for defining subsequent delivery of electrical stimulation therapy to the patient comprises selecting the second subset of the plurality of therapy parameter sets for defining subsequent delivery of electrical stimulation therapy to the patient.

17. The method of claim 11, further comprising delivering electrical stimulation therapy according to the selected at least one subset of the plurality of therapy parameter sets to the patient for a chronic period of time to treat the condition of the patient, wherein the electrical stimulation therapy is delivered according to the plurality of therapy parameter sets for a trial period of time shorter than the chronic period of time.

18. The method of claim 11, wherein the plurality of tissue sites of the patient comprise at least a T9 vertebrae region of a spinal cord of the patient or a T10 vertebrae region of the spinal cord of the patient.

19. The method of claim 11, wherein each therapy parameter set of the plurality of therapy parameter sets defines electrical stimulation therapy comprising at least first electrical stimulation pulses at a first frequency greater than about 600 Hertz and less than about 1,500 Hertz interleaved with second electrical stimulation pulses at a second frequency greater than about 600 Hertz and less than about 1,500 Hertz to form a pulse train with a pulse frequency of greater than approximately 1,500 Hertz.

20. The method of claim 11, wherein each therapy parameter set of the plurality of therapy parameter sets defines electrical stimulation therapy comprising electrical stimulation pulses comprising a pulse frequency greater than about 1000 Hz.

21. A non-transitory computer-readable storage medium comprising instructions that, when executed, cause processing circuitry to:
- control stimulation circuitry of a medical device to deliver, via a plurality of electrodes, electrical stimulation therapy according to a plurality of therapy parameter sets to a plurality of respective tissue sites of a patient, the electrical stimulation therapy configured to treat a condition of the patient, and wherein delivering the electrical stimulation therapy according to the plurality of therapy parameter sets comprises one of: simultaneously delivering the electrical stimulation therapy according to each therapy parameter set of the plurality of therapy parameter sets, or delivering the electrical stimulation therapy according to each therapy parameter set of the plurality of therapy parameter sets on a time-interleaved basis with other therapy parameter sets of the plurality of therapy parameter sets;
- subsequent to delivery of the electrical stimulation therapy according to the plurality of therapy parameter sets, select a plurality of subsets of the plurality of therapy parameter sets, wherein each subset of the plurality of therapy parameter sets includes at least one therapy parameter set of the plurality of therapy parameter sets and less than all of the plurality of therapy parameter sets, and wherein electrical stimulation therapy is delivered according to each subset of the plurality of therapy parameter sets via a respective set of electrodes different from sets of electrodes that deliver other subsets of the plurality of therapy parameter sets;
- iteratively control the stimulation circuitry to deliver electrical stimulation therapy according to the subsets of the plurality of therapy parameter sets to the patient via the respective sets of electrodes;
- determine, based on the iterative delivery of electrical stimulation therapy according to the subsets of the plurality of therapy sets, one or more subsets of the plurality of therapy parameters that treat the condition of the patient, wherein the one or more subsets are less than all of the subsets of the plurality of therapy parameter sets;
- select the one or more subsets of the plurality of therapy parameter sets for defining subsequent electrical stimulation therapy to the patient; and
- control the stimulation circuitry to deliver the subsequent electrical stimulation therapy to the patient according to the selected one or more subsets of the plurality of therapy parameter sets.

* * * * *